US011963792B1

(12) United States Patent
Kahn et al.

(10) Patent No.: US 11,963,792 B1
(45) Date of Patent: Apr. 23, 2024

(54) SLEEP ECOSYSTEM

(71) Applicants: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US); Steven D. Powell, Provo, UT (US)

(72) Inventors: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US); Steven D. Powell, Provo, UT (US)

(73) Assignee: DP Technologies, Inc., Scotts Valley, CA (US)

( * ) Notice: Subject to any disclaimer, the term of this patent is extended or adjusted under 35 U.S.C. 154(b) by 220 days.

(21) Appl. No.: 15/071,191

(22) Filed: Mar. 15, 2016

Related U.S. Application Data

(63) Continuation-in-part of application No. 14/469,509, filed on Aug. 26, 2014, now Pat. No. 10,568,565.

(60) Provisional application No. 62/133,990, filed on Mar. 16, 2015, provisional application No. 61/988,208, filed on May 4, 2014.

(51) Int. Cl.
*A61B 5/00* (2006.01)
*A61B 5/11* (2006.01)

(52) U.S. Cl.
CPC .......... *A61B 5/4812* (2013.01); *A61B 5/1126* (2013.01)

(58) Field of Classification Search
CPC ............................ A61B 5/4812; A61B 5/1126
See application file for complete search history.

(56) References Cited

U.S. PATENT DOCUMENTS

| | | |
|---|---|---|
| 2,082,843 A | 6/1937 | Mathez |
| 3,541,781 A | 11/1970 | Bloom |
| 3,683,933 A | 8/1972 | Mansfield |
| 3,798,889 A | 3/1974 | Chadwick |
| 4,228,806 A | 10/1980 | Lidow |
| 4,297,685 A | 10/1981 | Brainard, II |
| 4,322,609 A | 3/1982 | Kato |
| 4,573,804 A | 3/1986 | Kavoussi et al. |
| 4,788,533 A | 11/1988 | Mequignon |

(Continued)

FOREIGN PATENT DOCUMENTS

| | | |
|---|---|---|
| AU | 2003203967 A1 | 11/2004 |
| CH | 377738 A | 1/1964 |

(Continued)

OTHER PUBLICATIONS

"Fitbit Product Manual,", Last updated Mar. 29, 2010, 20 pages.

(Continued)

*Primary Examiner* — Alex M Valvis
*Assistant Examiner* — Justin Xu
(74) *Attorney, Agent, or Firm* — Nicholson De Vos Webster & Elliott LLP; Judith Szepesi

(57) ABSTRACT

Devices, systems and methods that track various aspects of a person's sleep and environment to optimize one or more aspects of the user's environment and sleep conditions, quality and duration, together or alone, and help make the one or more users maintain and prolong his or her deep sleep status and improve the their sleep duration and quality.

6 Claims, 10 Drawing Sheets

(56) References Cited

U.S. PATENT DOCUMENTS

| | | | |
|---|---|---|---|
| 4,848,360 A | 7/1989 | Palsgard et al. |
| 4,858,609 A | 8/1989 | Cole |
| 4,982,738 A | 1/1991 | Griebel |
| 5,008,865 A | 4/1991 | Shaffer et al. |
| 5,047,930 A | 9/1991 | Martens et al. |
| 5,168,759 A | 12/1992 | Bowman |
| 5,275,159 A | 1/1994 | Griebel |
| 5,335,657 A | 8/1994 | Terry, Jr. et al. |
| 5,458,105 A | 10/1995 | Taylor et al. |
| 5,545,192 A | 8/1996 | Czeisler et al. |
| 5,562,106 A | 10/1996 | Heeke et al. |
| 5,671,733 A | 9/1997 | Raviv et al. |
| 5,844,996 A | 12/1998 | Enzmann et al. |
| 5,868,647 A | 2/1999 | Belsole |
| 5,928,133 A | 7/1999 | Halyak |
| 5,961,447 A | 10/1999 | Raviv et al. |
| 6,014,682 A | 1/2000 | Stephen et al. |
| 6,045,514 A | 4/2000 | Raviv et al. |
| 6,231,527 B1 | 5/2001 | Sol |
| 6,239,706 B1 | 5/2001 | Yoshiike et al. |
| 6,350,275 B1 | 2/2002 | Vreman et al. |
| 6,361,508 B1 | 3/2002 | Johnson et al. |
| 6,468,234 B1 | 10/2002 | Van der Loos et al. |
| 6,547,728 B1 | 4/2003 | Cornuejols |
| 6,556,222 B1 | 4/2003 | Narayanaswami |
| 6,834,436 B2 | 12/2004 | Townsend et al. |
| 6,888,779 B2 | 5/2005 | Mollicone et al. |
| 6,928,031 B1 | 8/2005 | Kanevsky et al. |
| 6,963,271 B1 | 11/2005 | Fyffe |
| 7,006,650 B1 | 2/2006 | Wild |
| 7,041,049 B1 | 5/2006 | Raniere |
| 7,106,662 B1 | 9/2006 | Acker |
| 7,139,342 B1 | 11/2006 | Phanse |
| 7,153,278 B2 | 12/2006 | Ono et al. |
| 7,280,439 B1 | 10/2007 | Shaddox |
| 7,366,572 B2 | 4/2008 | Heruth et al. |
| 7,513,003 B2 | 4/2009 | Mossbeck |
| 7,559,903 B2 | 7/2009 | Moussavi et al. |
| 7,572,225 B2 | 8/2009 | Stahmann et al. |
| 7,652,581 B2 | 1/2010 | Gentry et al. |
| 7,841,987 B2 | 11/2010 | Sotos et al. |
| 7,862,226 B2 | 1/2011 | Bracher et al. |
| 7,868,757 B2 | 1/2011 | Radivojevic et al. |
| 7,914,468 B2 | 3/2011 | Shalon et al. |
| 7,974,849 B1 | 7/2011 | Begole et al. |
| 8,179,270 B2 | 5/2012 | Rai et al. |
| 8,193,941 B2 | 6/2012 | Wolfe et al. |
| 8,398,546 B2 | 3/2013 | Pacione et al. |
| 8,407,835 B1 | 4/2013 | Connor |
| 8,475,339 B2 | 7/2013 | Hwang et al. |
| 8,482,418 B1 | 7/2013 | Harman |
| 8,577,448 B2 | 11/2013 | Bauer et al. |
| 8,680,974 B2 | 3/2014 | Meiertoberens et al. |
| 8,738,925 B1 | 5/2014 | Park et al. |
| 8,892,036 B1 | 11/2014 | Causey et al. |
| 8,909,357 B2 | 12/2014 | Rawls-Meehan |
| 8,942,719 B1 | 1/2015 | Hyde et al. |
| 9,060,735 B2 | 6/2015 | Yang et al. |
| 9,161,719 B2 | 10/2015 | Tsutsumi et al. |
| 9,257,029 B1 | 2/2016 | Hendrick et al. |
| 9,448,536 B1 | 9/2016 | Kahn et al. |
| 9,474,876 B1 | 10/2016 | Kahn et al. |
| 9,594,354 B1 | 3/2017 | Kahn et al. |
| 9,675,268 B2 | 6/2017 | Bauer et al. |
| 9,844,336 B2 | 12/2017 | Zigel et al. |
| 10,004,452 B2 | 6/2018 | Kazem-Moussavi et al. |
| 10,207,075 B1 | 2/2019 | Kahn et al. |
| 10,252,058 B1 | 4/2019 | Fuerst |
| 10,335,060 B1 | 7/2019 | Kahn et al. |
| 10,842,968 B1 | 11/2020 | Kahn et al. |
| 11,100,922 B1 | 8/2021 | Mutagi et al. |
| 2001/0049482 A1 | 12/2001 | Pozos et al. |
| 2002/0080035 A1 | 6/2002 | Youdenko |
| 2002/0100477 A1 | 8/2002 | Sullivan et al. |
| 2002/0124848 A1 | 9/2002 | Sullivan et al. |
| 2003/0095476 A1 | 5/2003 | Vollicone et al. |
| 2003/0204412 A1 | 10/2003 | Brier |
| 2003/0227439 A1* | 12/2003 | Lee ............... H05B 47/175 345/156 |
| 2003/0231495 A1 | 12/2003 | Searfoss |
| 2004/0034289 A1 | 2/2004 | Teller et al. |
| 2004/0049132 A1 | 3/2004 | Barron et al. |
| 2004/0071382 A1 | 4/2004 | Rich et al. |
| 2004/0111039 A1 | 6/2004 | Minamiura et al. |
| 2004/0133081 A1 | 7/2004 | Teller et al. |
| 2004/0210155 A1 | 10/2004 | Takemura et al. |
| 2004/0218472 A1 | 11/2004 | Narayanaswami et al. |
| 2005/0012622 A1 | 1/2005 | Sutton |
| 2005/0043645 A1 | 2/2005 | Ono et al. |
| 2005/0075116 A1 | 4/2005 | Laird et al. |
| 2005/0076715 A1 | 4/2005 | Kuklis et al. |
| 2005/0143617 A1 | 6/2005 | Auphan |
| 2005/0154330 A1 | 7/2005 | Loree |
| 2005/0190065 A1 | 9/2005 | Ronnholm |
| 2005/0236003 A1 | 10/2005 | Meader |
| 2005/0237479 A1 | 10/2005 | Rose |
| 2005/0245793 A1 | 11/2005 | Hilton et al. |
| 2005/0283039 A1 | 12/2005 | Cornel |
| 2005/0288904 A1 | 12/2005 | Warrior et al. |
| 2006/0017560 A1 | 1/2006 | Albert |
| 2006/0025299 A1 | 2/2006 | Miller et al. |
| 2006/0064037 A1 | 3/2006 | Shalon et al. |
| 2006/0097884 A1 | 5/2006 | Jang et al. |
| 2006/0136018 A1 | 6/2006 | Lack et al. |
| 2006/0150734 A1 | 7/2006 | Mimnagh-Kelleher et al. |
| 2006/0252999 A1 | 11/2006 | DeVaul et al. |
| 2006/0266356 A1 | 11/2006 | Sotos et al. |
| 2006/0279428 A1 | 12/2006 | Sato et al. |
| 2006/0293602 A1 | 12/2006 | Clark |
| 2006/0293608 A1 | 12/2006 | Rothman et al. |
| 2007/0016091 A1 | 1/2007 | Butt et al. |
| 2007/0016095 A1 | 1/2007 | Low et al. |
| 2007/0093722 A1 | 4/2007 | Noda et al. |
| 2007/0100666 A1 | 5/2007 | Stivoric et al. |
| 2007/0129644 A1 | 6/2007 | Richards et al. |
| 2007/0139362 A1 | 6/2007 | Colton et al. |
| 2007/0191692 A1 | 8/2007 | Hsu et al. |
| 2007/0239225 A1 | 10/2007 | Saringer |
| 2007/0250286 A1 | 10/2007 | Duncan et al. |
| 2007/0251997 A1 | 11/2007 | Brown et al. |
| 2007/0287930 A1 | 12/2007 | Sutton |
| 2008/0062818 A1 | 3/2008 | Plancon et al. |
| 2008/0109965 A1 | 5/2008 | Mossbeck |
| 2008/0125820 A1 | 5/2008 | Stahmann et al. |
| 2008/0169931 A1 | 7/2008 | Gentry et al. |
| 2008/0191885 A1 | 8/2008 | Iv et al. |
| 2008/0234785 A1 | 9/2008 | Nakayama et al. |
| 2008/0243014 A1 | 10/2008 | Moussavi et al. |
| 2008/0269625 A1 | 10/2008 | Halperin et al. |
| 2008/0275348 A1 | 11/2008 | Catt et al. |
| 2008/0275349 A1 | 11/2008 | Halperin et al. |
| 2008/0289637 A1 | 11/2008 | Wyss |
| 2008/0319277 A1 | 12/2008 | Bradley |
| 2009/0030767 A1 | 1/2009 | Morris et al. |
| 2009/0048540 A1 | 2/2009 | Otto et al. |
| 2009/0069644 A1 | 3/2009 | Hsu et al. |
| 2009/0071810 A1 | 3/2009 | Hanson et al. |
| 2009/0082699 A1 | 3/2009 | Bang et al. |
| 2009/0094750 A1 | 4/2009 | Oguma et al. |
| 2009/0105785 A1 | 4/2009 | Wei et al. |
| 2009/0121826 A1 | 5/2009 | Song et al. |
| 2009/0128487 A1 | 5/2009 | Langereis et al. |
| 2009/0143636 A1 | 6/2009 | Mullen et al. |
| 2009/0150217 A1 | 6/2009 | Luff |
| 2009/0177327 A1 | 7/2009 | Turner et al. |
| 2009/0203970 A1 | 8/2009 | Fukushima et al. |
| 2009/0203972 A1* | 8/2009 | Heneghan ............ G16H 40/63 600/301 |
| 2009/0207028 A1 | 8/2009 | Kubey et al. |
| 2009/0227888 A1 | 9/2009 | Salmi et al. |
| 2009/0264789 A1 | 10/2009 | Molnar et al. |
| 2009/0320123 A1* | 12/2009 | Yu ............... H04W 12/0605 726/16 |
| 2010/0010330 A1 | 1/2010 | Rankers et al. |

(56) References Cited

U.S. PATENT DOCUMENTS

| | | |
|---|---|---|
| 2010/0010565 A1 | 1/2010 | Lichtenstein et al. |
| 2010/0036211 A1 | 2/2010 | La et al. |
| 2010/0061596 A1 | 3/2010 | Mostafavi et al. |
| 2010/0075807 A1 | 3/2010 | Hwang et al. |
| 2010/0079291 A1 | 4/2010 | Kroll et al. |
| 2010/0079294 A1 | 4/2010 | Rai et al. |
| 2010/0083968 A1 | 4/2010 | Wondka et al. |
| 2010/0094139 A1 | 4/2010 | Brauers et al. |
| 2010/0094148 A1 | 4/2010 | Bauer et al. |
| 2010/0100004 A1 | 4/2010 | Someren |
| 2010/0102971 A1 | 4/2010 | Virtanen et al. |
| 2010/0152543 A1 | 6/2010 | Heneghan et al. |
| 2010/0152546 A1 | 6/2010 | Behan et al. |
| 2010/0217146 A1 | 8/2010 | Osvath |
| 2010/0256512 A1 | 10/2010 | Sullivan |
| 2010/0283618 A1 | 11/2010 | Wolfe et al. |
| 2010/0331145 A1 | 12/2010 | Lakovic et al. |
| 2011/0015467 A1* | 1/2011 | Dothie .......... A61B 5/6887 600/26 |
| 2011/0015495 A1 | 1/2011 | Dothie et al. |
| 2011/0018720 A1 | 1/2011 | Rai et al. |
| 2011/0046498 A1 | 2/2011 | Klap et al. |
| 2011/0054279 A1 | 3/2011 | Reisfeld et al. |
| 2011/0058456 A1 | 3/2011 | De et al. |
| 2011/0090226 A1 | 4/2011 | Sotos et al. |
| 2011/0105915 A1 | 5/2011 | Bauer et al. |
| 2011/0137836 A1 | 6/2011 | Kuriyama et al. |
| 2011/0160619 A1 | 6/2011 | Gabara |
| 2011/0190594 A1 | 8/2011 | Heit et al. |
| 2011/0199218 A1 | 8/2011 | Caldwell et al. |
| 2011/0230790 A1 | 9/2011 | Kozlov |
| 2011/0245633 A1 | 10/2011 | Goldberg et al. |
| 2011/0295083 A1 | 12/2011 | Doelling et al. |
| 2011/0302720 A1 | 12/2011 | Yakam et al. |
| 2011/0304240 A1 | 12/2011 | Meitav et al. |
| 2012/0004749 A1 | 1/2012 | Abeyratne et al. |
| 2012/0083715 A1 | 4/2012 | Yuen et al. |
| 2012/0232414 A1 | 9/2012 | Mollicone et al. |
| 2012/0243379 A1 | 9/2012 | Balli |
| 2012/0253220 A1 | 10/2012 | Rai et al. |
| 2012/0296156 A1* | 11/2012 | Auphan .......... A61M 21/02 600/26 |
| 2013/0012836 A1 | 1/2013 | Veiga et al. |
| 2013/0018284 A1 | 1/2013 | Kahn et al. |
| 2013/0023214 A1 | 1/2013 | Wang et al. |
| 2013/0053653 A1 | 2/2013 | Cuddihy et al. |
| 2013/0053656 A1 | 2/2013 | Mollicone et al. |
| 2013/0060306 A1 | 3/2013 | Colbauch |
| 2013/0144190 A1 | 6/2013 | Bruce et al. |
| 2013/0184601 A1 | 7/2013 | Zigel et al. |
| 2013/0197857 A1 | 8/2013 | Lu et al. |
| 2013/0204314 A1 | 8/2013 | Miller et al. |
| 2013/0208576 A1 | 8/2013 | Loree et al. |
| 2013/0283530 A1 | 10/2013 | Main et al. |
| 2013/0286793 A1 | 10/2013 | Umamoto |
| 2013/0289419 A1 | 10/2013 | Berezhnyy et al. |
| 2013/0300204 A1 | 11/2013 | Partovi |
| 2013/0310658 A1 | 11/2013 | Ricks et al. |
| 2013/0344465 A1 | 12/2013 | Dickinson et al. |
| 2014/0005502 A1 | 1/2014 | Klap et al. |
| 2014/0051938 A1 | 2/2014 | Goldstein et al. |
| 2014/0085077 A1 | 3/2014 | Luna et al. |
| 2014/0135955 A1 | 5/2014 | Burroughs |
| 2014/0171815 A1 | 6/2014 | Yang et al. |
| 2014/0200691 A1 | 7/2014 | Lee et al. |
| 2014/0207292 A1 | 7/2014 | Ramagem et al. |
| 2014/0218187 A1 | 8/2014 | Chun et al. |
| 2014/0219064 A1 | 8/2014 | Filipi et al. |
| 2014/0232558 A1 | 8/2014 | Park et al. |
| 2014/0256227 A1 | 9/2014 | Aoki et al. |
| 2014/0259417 A1 | 9/2014 | Nunn et al. |
| 2014/0259434 A1 | 9/2014 | Nunn et al. |
| 2014/0276227 A1 | 9/2014 | Pérez |
| 2014/0288878 A1 | 9/2014 | Donaldson |
| 2014/0306833 A1* | 10/2014 | Ricci .......... B60R 25/00 340/901 |
| 2014/0350351 A1 | 11/2014 | Halperin et al. |
| 2014/0371635 A1 | 12/2014 | Shinar et al. |
| 2015/0015399 A1 | 1/2015 | Gleckler et al. |
| 2015/0068069 A1 | 3/2015 | Tran et al. |
| 2015/0073283 A1 | 3/2015 | Vugt et al. |
| 2015/0085622 A1 | 3/2015 | Carreel et al. |
| 2015/0094544 A1 | 4/2015 | Spolin et al. |
| 2015/0098309 A1 | 4/2015 | Adams et al. |
| 2015/0101870 A1 | 4/2015 | Gough et al. |
| 2015/0136146 A1 | 5/2015 | Hood et al. |
| 2015/0141852 A1 | 5/2015 | Dusanter et al. |
| 2015/0148621 A1 | 5/2015 | Sier |
| 2015/0148871 A1 | 5/2015 | Maxik et al. |
| 2015/0164238 A1 | 6/2015 | Benson et al. |
| 2015/0164409 A1 | 6/2015 | Benson et al. |
| 2015/0164438 A1 | 6/2015 | Halperin et al. |
| 2015/0173671 A1 | 6/2015 | Paalasmaa et al. |
| 2015/0178362 A1 | 6/2015 | Wheeler |
| 2015/0190086 A1 | 7/2015 | Chan et al. |
| 2015/0220883 A1 | 8/2015 | Lingg et al. |
| 2015/0233598 A1 | 8/2015 | Shikii et al. |
| 2015/0238139 A1 | 8/2015 | Raskin et al. |
| 2015/0265903 A1 | 9/2015 | Kolen et al. |
| 2015/0289802 A1 | 10/2015 | Thomas et al. |
| 2015/0320588 A1* | 11/2015 | Connor .......... A61F 7/0085 607/104 |
| 2015/0333950 A1 | 11/2015 | Johansson |
| 2015/0346824 A1 | 12/2015 | Chen et al. |
| 2015/0351694 A1 | 12/2015 | Shimizu et al. |
| 2016/0015315 A1 | 1/2016 | Auphan et al. |
| 2016/0045035 A1 | 2/2016 | Van Erlach |
| 2016/0217672 A1 | 7/2016 | Yoon et al. |
| 2016/0262693 A1 | 9/2016 | Sheon |
| 2016/0287869 A1 | 10/2016 | Errico et al. |
| 2017/0003666 A1 | 1/2017 | Nunn et al. |
| 2017/0020756 A1 | 1/2017 | Hillenbrand et al. |
| 2017/0188938 A1 | 7/2017 | Toh et al. |
| 2018/0049701 A1 | 2/2018 | Raisanen |
| 2018/0103770 A1 | 4/2018 | Nava et al. |
| 2018/0338725 A1 | 11/2018 | Shan et al. |
| 2019/0021675 A1 | 1/2019 | Gehrke et al. |
| 2019/0044380 A1 | 2/2019 | Lausch et al. |
| 2019/0132570 A1 | 5/2019 | Chen et al. |
| 2019/0156296 A1 | 5/2019 | Lu et al. |
| 2019/0190992 A1 | 6/2019 | Warrick |
| 2019/0201270 A1 | 7/2019 | Sayadi et al. |

FOREIGN PATENT DOCUMENTS

| | | |
|---|---|---|
| CH | 668349 A | 12/1988 |
| CH | 697528 B1 | 11/2008 |
| DE | 4101471 A1 | 7/1992 |
| DE | 19642316 A1 | 4/1998 |
| EP | 1139187 A3 | 11/2005 |
| JP | 8160172 | 6/1996 |
| JP | 2007132581 A | 5/2007 |
| KR | 1020100022217 A | 3/2010 |
| KR | 1020009085403 | 6/2011 |
| WO | 93/02731 A1 | 2/1993 |
| WO | 2008038288 A3 | 5/2009 |
| WO | 2009099292 A2 | 8/2009 |
| WO | 2011141840 A1 | 11/2011 |

OTHER PUBLICATIONS

"How BodyMedia FIT Works", , accessed Jun. 17, 2011, 2 pages.
"Power Nap," , Last Modified Sep. 20, 2012, 4 pages.
"Sara Mednick," , Last Modified Sep. 12, 2012, 2 pages.
"Sleep Debt," , Last Modified Aug. 25, 2012, 3 pages.
"Sleep Inertia," , Last Modified Sep. 12, 2012, 2 pages.
"Sleep," , Last Modified Oct. 5, 2012, 21 pages.
"Slow Wave Sleep," , Last Modified Jul. 22, 2012, 4 pages.
Actigraphy, From Wikipedia, the free encyclopedia, downloaded at: http://en.wikipedia.org/wiki/Actigraphy on Apr. 24, 2014, 4 pages.
David F. Dinges, , Last Modified Sep. 12, 2012, 2 pages.

(56) References Cited

OTHER PUBLICATIONS

Desai, Rajiv, The Sleep, Archive for Mar. 2011, Dr. Rajiv Desai Blog, Mar. 17, 2011, 46 pages.
Sunseri, Maria, et al., "The SenseWear (TM) Armband as a Sleep Detection Device," <http://sensewear.bodymedia.com/SenseWear-Studies/SW-Whitepapers/The-SenseWear-armband-as-a-Sleep-Detection-Device>, 2005, 9 pages.
Jaines, Kira, "Music to Help You Fall Sleep," <http://www.livestrong.com/article/119802-music-fall-sleep/>, May 10, 2010, 2 pages.
Jetlog Reviewers Guide, , 2009, 5 pages.
Lichstein, et al., Actigraphy Validation with Insomnia, Sleep, vol. 29, No. 2, 2006, pp. 232-239.
Iden, Craig B, et al., "Characterization and Implications of the Sensors Incorporated into the SenseWear(TM) Armband for Energy Expenditure and Activity Detection", , accessed Jun. 17, 2011, 7 pages.
Patel, et al., Validation of Basis Science Advanced Sleep Analysis, Estimation of Sleep Stages and Sleep Duration, Basis Science, San Francisco, CA, Jan. 2014, 6 pages.
Pires, P. D. C. Activity Characterization from Actimetry Sensor Data for Sleep Disorders Diagnosis, Universidade Técnica de Lisboa, Sep. 2008, 10 pages.
Pollak, et al., How Accurately Does Wrist Actigraphy Identify the States of Sleep and Wakefulness?, Actigraphy and Sleep, Sleep, vol. 24, No. 8, 2001, pp. 957-965.
PowerNap iPhone App, , Jan. 6, 2010, 10 pages.
Sound-Remedies.com: Sonic Solutions for Health, Learning & Productivity, <http://www.sound-remedies.com/ammusforslee.html>, Accessed May 23, 2013, 2 pages.
Haughton Mifflin, "Estimate", The American Heritage dictionary of the English language (5th ed.), Jul. 24, 2017, 2 pages.
Mattila et al., "A Concept for Personal Wellness Management Based on Activity Monitoring," Pervasive Computing Technologies for Healthcare, 2008.
Notice of Allowance, U.S. Appl. No. 14/918,540, dated Feb. 22, 2021, 8 pages.
Rechtschaffen et al., Manual of Standardized Terminology, Techniques and Scoring System for Sleep Stages of Human Subjects, 1968, 57 pages.
Schulz et al. "Phase shift in the REM sleep rhythm." Pflugers Arch. 358, 1975, 10 pages.
Schulz et al. "The REM-NREM sleep cycle: Renewal Process or Periodically Driven Process?." Sleep, 1980, pp. 319-328.
Yassourdidis et al. "Modelling and Exploring Human Sleep with Event History Analysis." Journal of Sleep Research, 1999, pp. 25-36.
"NPL—EasySense LTD", archive.org, accessed: Jan. 7, 2019, published: Nov. 27, 2006.
Advisory Action, U.S. Appl. No. 17/647,160, dated Jan. 10, 2023, 3 pages.
Campbell, Appleinsider, "Apple buys sleep tracking firm Beddit" May 9, 2017. Retrieved from https://appleinsider.com/articles/May 17, 09/apple-buys-sleep-tracking-firm-beddit (Year: 2017).
Crist, CNET "Samsung introduces SleepSense" Sep. 3, 2015. Retrieved from https://www.cnet.com/reviews/samsung-sleepsense-preview (Year: 2015).
Final Offce Action, U.S. App. No. 15/071,189, dated Nov. 28, 2022, 22 pages.
Final Offce Action, U.S. App. No. 16/799,786, dated Dec. 9, 2022, 16 pages.
Internet Archive, Withings "Sleep Tracking Mat" Nov. 22, 2018. Retrieved from https://web.archive.org/web/20181122024547/https://www.withings.com/US/en/sleep (Year: 2018).
Ding, F., et al., "Polysomnographic validation of an under-mattress monitoring device in estimating sleep architecture and obstructive sleep apnea in adults," Sleep Medicine, vol. 96, Apr. 2022, pp. 20-27.

\* cited by examiner

SLEEP ECOSYSTEM

RELATED APPLICATION

This application is a continuation-in-part of U.S. patent application Ser. No. 14/469,509, filed on Aug. 26, 2014, which claims priority to U.S. Provisional Application No. 61/988,208, filed on May 3, 2014, and also claims priority to U.S. Provisional Application No. 62/133,990, filed on Mar. 16, 2015, all of which prior applications are incorporated herein by reference in their entirety.

BACKGROUND

An average person spends about one-third of his or her life asleep. Sleep is the time our bodies undergo repair and detoxification. Research has shown that poor sleep patterns are an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five sleep cycles, each lasting about 90 minutes. In general, each sleep cycle includes four stages, NREM1, NREM2, NREM3, and REM. The first four stages of each cycle are often regarded as quiet sleep or non-rapid eye movement (NREM), and are typically NREM1, NREM2, NREM3, followed by NREM2. The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

During a sleep, the person's body temperature will also continue to fall throughout the night. For instance, often a person's body temperature during the early morning (e.g., around 5:00 am) is usually one degree centigrade below his or her body temperature the evening before when they first went to sleep. Lower body temperature is believed to assist in and/or linked to deep/restorative sleep that allows the body a chance to rest and rebuild itself. As body temperature rises, deep sleep is more difficult to achieve and maintain.

BRIEF SUMMARY

The presently disclosed embodiments, as well as features and aspects thereof, are directed towards a system and method for identifying a sleep ecosystem using a plurality of sensors. In one embodiment, an area motion sensor is used. An area motion sensor is a motion sensor that does not rely on being in contact with the user. The area motion sensor in one embodiment is one of a passive infrared (PIR), proximity sensor (using radio waves, ultraviolet, or other sensors), microwave/radar sensor, area reflective sensor, ultrasonic sensor, or video motion sensor. In one embodiment, the area motion sensor is a digital sensor, such as a passive infrared sensor (PIR sensor), which indicates motion or lack of motion. In another embodiment, an inductive sensor integrated with the sleep surface is used.

BRIEF DESCRIPTION OF THE DRAWINGS

In the Figures, like reference numerals refer to like parts throughout the various views unless otherwise indicated.

DETAILED DESCRIPTION

Figure 1A:
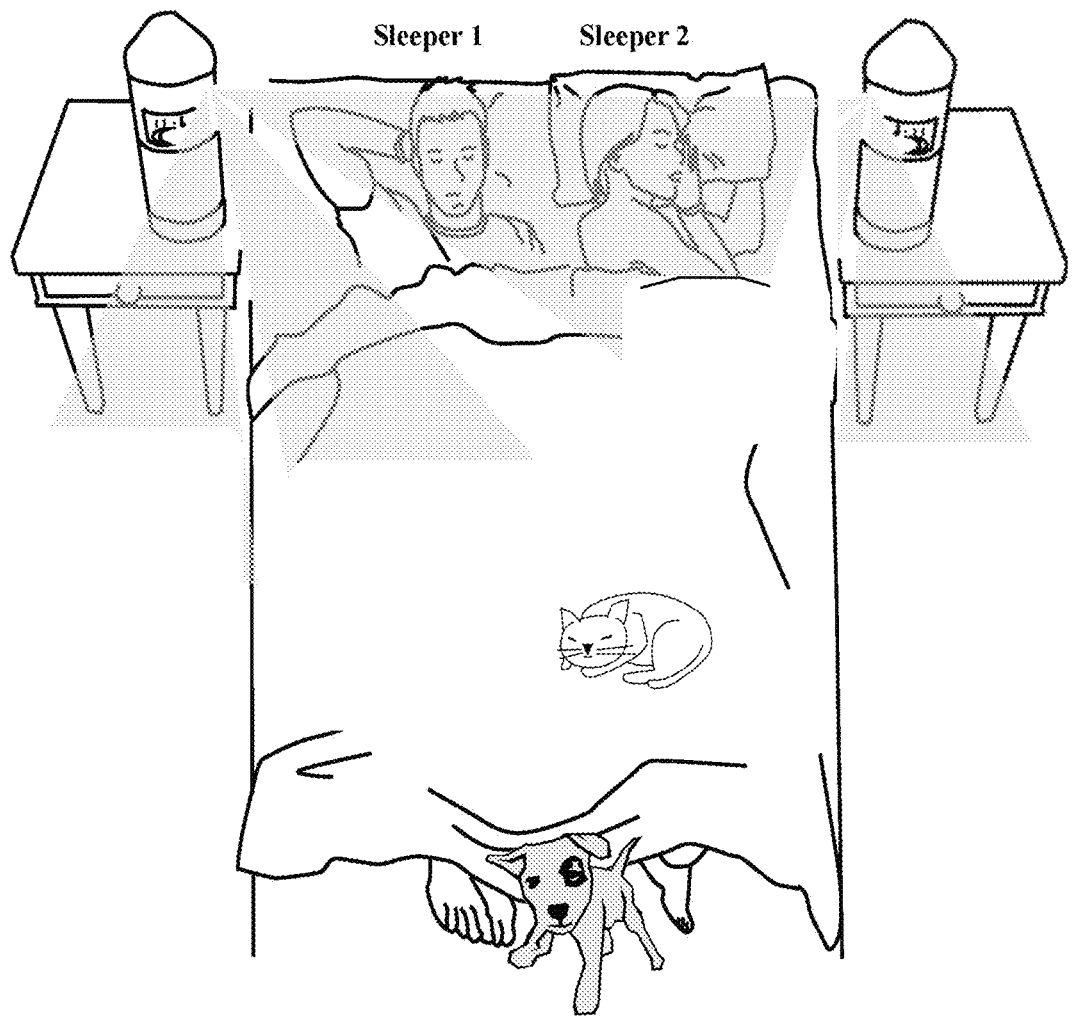
FIG. 1A is an illustration of an exemplary embodiment showing sleep tracking system for a sleep ecosystem.

The presently disclosed embodiments, as well as features and aspects thereof, are directed towards defining a sleep ecosystem, and addressing the sleep quality of one or more family members in the sleep ecosystem. A sleep ecosystem can include a plurality of human and non-human family members in the same environment for sleeping. For example, typically married couples share a bed. Some families sleep with pets on the bed. Some families sleep with children, etc. The definition of the sleep ecosystem encompasses the human and non-human family members, in the environment. Of course in this context "family" encompasses human and non-human creatures who share a sleeping environment, and no legal or biological relationship is meant to be implied between the parties. The system in one embodiment determines each individual's sleep phase in the sleep ecosystem, and attempts to optimize the environment for the family members. In one embodiment, a plurality of passive and/or active sensors may be used for this determination.

The sleep tracking system may be used to improve the sleep environment, maximize family members' deep sleep and create a customizable environment and program for the sleep ecosystem based on what works for the family members in the sleep ecosystem. This may be done, in one embodiment, by monitoring and analyzing the sleep duration, quality and stage for the human family members in the sleep ecosystem. In one embodiment, in addition to an area motion sensor, the sleep tracking system may include other sensors, which provide further data. The sleep tracking system can be utilized to maximize a user's sleep quality, by monitoring and analyzing the user's sleep stage and adjusting the user's sleep environment.

In one embodiment, the sleep tracking system is completely non-invasive and it requires are no awkward external components to monitor sleep. This is possible using area motion-sensor technology used with sensor-fusion and machine learning. The user experience is radically simplified. The sleep tracking system correlates the input from its array of sensors using advanced machine learning technology to define the sleep ecosystem and determine the sleep state of the family members. This data is used to adjust the environment to help the family members fall asleep faster, wake the relevant user(s) up at the optimal time in his or her sleep cycle so they feel more refreshed.

The sleep tracking system may use an inductive sensor built into the bedframe, mattress, or box spring. This system also does not require configuration by the user and provides a simple and natural interaction model.

The term "family member" and sleep ecosystem are used throughout this application. The term "family member" refers to any person or animal that shares the sleep area that is defined by the sleep ecosystem. Though the term "family" is used, it is simply a shorthand used to define the people and animals who are sharing the sleeping space, there is no implication of a familial relationship. The sleep ecosystem may encompass a space as large as a house, a room, or small as a bed, shared by one or more family members. In one embodiment, in a home with multiple sleeping areas, separate monitoring systems may exist in each sleeping area, and the separate systems may wirelessly communicate. In one embodiment, the system tracks and optimizes the sleep of only the human family members. However, the movements and comfort of the non-human family members are also part of the sleep ecosystem, as everyone impacts each other. Alternatively, the system may attempt to optimize for all family members.

In one embodiment, the system may also be used in a smart home environment to put other aspects of the home into sleep mode when it is detected that all family members are asleep, to turn off lights, lock doors, adjust house temperatures, etc. In one embodiment, the system may also use the detection of the sleep state, to place a wearable device, worn by the user, into sleep mode automatically. This may be used to enable the wearable device to monitor the user's sleep, to provide more data, in one embodiment. In one embodiment, this may be used to reduce power consumption by the wearable device, when other sensors, such as the area motion sensor, are monitoring the user's sleep, and the additional data is not needed. In one embodiment, the area motion sensor may place the wearable device in sleep monitoring mode or non-monitoring mode, as needed. In one embodiment, if the sleep tracking system cannot monitor the user's sleep state using the area motion sensor, it may enable the wearable sensor to add additional data. In one embodiment, the sleep tracking system may interface with these external elements through an intermediary, such as a smart house system, a smart phone, or a computer.

The sleep tracking system in one embodiment monitors and understands sleep interruptions (snoring, apnea, ambulance siren, trips to the bathroom, etc.). In one embodiment, an area motion sensor includes a smart reading light that knows when the user is falling asleep and initiates a lighting sequence that helps the user fall asleep faster when they choose to. In one embodiment, the sleep tracking system can also tap into the user's music and sound selection to create a calming and relaxed ambience for falling asleep faster. Similarly, in one embodiment, the sleep tracking system may use a waking lighting sequence and appropriate music and sounds to help the user wake up refreshed, when waking is detected or based on an alarm setting. In one embodiment, the system may enable the user to, or automatically customize the sleeping and waking sounds, lights, and other conditions based on the family members in the sleep ecosystem. In one embodiment, the system may include body-worn device such as a wristband, which may be used to wake a family member if the remaining sleepers in the sleep ecosystem could remain asleep.

The sleep tracking system, in one embodiment, also monitors the air quality and temperature to alert the user of unhealthy conditions and monitor correlations with sleep quality. Additional local conditions may also be monitored, and adjusted when appropriate, in one embodiment.

In one embodiment, the sleep tracking system also taps into the smart home's controls, and can extend its reach to interface with other home controls. This type of Internet of Things (IoT) access to other elements which may be remotely controlled can make the sleep tracking system an essential part of the home IoT environment. For example, in some embodiments, the sleep tracking system can interface with thermostats, lock doors, dim or turn on & off lights, control music, and even turn on the coffee maker in the morning.

Throughout the description, various embodiments will be referred to as an embodiment and the use of such term is not meant to be limiting but rather encompassing of all of the various embodiments, features and aspects thereof, as well as other anticipated embodiments. The word "exemplary" is used herein to mean "serving as an example, instance-, or illustration." Any aspect described herein as "exemplary" is not necessarily to be construed as exclusive, preferred or advantageous over other aspects. Though embodiments are all presented as "in one embodiment," such embodiments are not mutually exclusive or mutually inclusive, nor are features described required.

The sleep tracking system described uses an area motion sensor, in one embodiment. An area motion sensor is a motion sensor that does not rely on being in contact with the user directly or indirectly. Exemplary area motion sensors include passive infrared (PIR), proximity sensor (using radio waves, ultraviolet, or other sensors), microwave/radar sensor, area reflective sensor, ultrasonic sensor, video motion sensor. In one embodiment, the area motion sensor is a digital sensor, such as a passive infrared sensor (PIR sensor), which indicates motion or lack of motion only. Area sensors are generally digital, and have two states, triggered and not triggered, aka on or off. The ability to use such simple digital sensors to correctly determine the user's sleep phase would normally be considered impossible. However, the system described herein has this capability. By using an area motion sensor, rather than an accelerometer, no interaction with the user is required to activate or control the system. There is nothing that requires charging, plugging in, downloading, etc. There is nothing to lose, or misplace. Rather, the sleep tracking device can simply sit on the user's night stand, or elsewhere in the sleeping area, and monitor the user(s). Additionally, the sensor is lower cost, and more reliable.

In one embodiment, the sleep tracking system may use an inductive sensor underneath a mattress, or as part of a box spring to detect motions in the sleep ecosystem. Such as system is described in co-pending application U.S. patent application Ser. No. XYZ, filed concurrently herewith, with the title "Sleep Surface Sensor Based Sleep Analysis System." That application is incorporated herein in its entirety. The system uses predictive logic and analytics to identify the various family members associated with the motion data, and separate their data to provide analytics for each member of the family. Other methods of obtaining movement data may be utilized. The inductive sensor is coupled to a device plugged into the wall, which requires no interaction with the user to active or control the system, nor does it require charging, plugging in, downloading, or other interactions.

The device may automatically send data to the user's mobile device once paired. Thus, the user can ignore the mechanics of the monitoring entirely, and need not be concerned about ensuring that the device is worn, charged, etc.

In one embodiment, as shown in FIG. 1A, a sleep tracking device comprises two devices, each with one or more beams. Each area motion sensor beam has a range in which the sensor would be triggered. Each of the area motion sensors detects at least two different states (i.e., one state for movement and one state for non-movement). Three area motion sensor beams with two states each can provide eight different logical combinations. Furthermore, the historical data and the timing between the sensors being triggered adds additional information. Using the data from area motion sensors, shown in FIG. 1A, the system is capable of identifying the user's sleep state. In one embodiment, the system may use the sleep state data to adjust the user's environment, to optimize for sleep quality. As can be seen, in FIG. 1A, the sleep ecosystem may include one or more humans and animals. Because the sleep and waking of everyone in the sleep ecosystem impacts the sleep and waking of everyone else in the sleep ecosystem, the system in one embodiment tracks the movement of everyone in the sleep ecosystem.

In one embodiment, the sleep tracking device may include technology for monitoring a user to identify the movement of the humans in the sleep ecosystem through sleep cycles. Embodiments may be implemented in a sleep tracking device that can sit on a user's night stand, hang on the wall in the user's room, attach to the user's bed post or headboard, be incorporated into a device or structure in the home or used by the user, part of a mattress or box spring, a combination of multiple devices, or any other method or device that is known to one of one of ordinary skill in the art. In one embodiment, the sleep tracking device is designed to be plugged in, and used as a combination sleep tracking device, alarm clock, reading light, and/or night light. In one embodiment, the sleep tracking device may be part of a sleep tracking system which may also include a motion sensors, such as an accelerometer or gyroscope to measure the user's motion more directly, other sensors and/or devices.

The area motion sensor, in some embodiments, transmits signals in the direction of the user and receives bounce backs or echoes of the signals. The transmitted signals can be ultrasonic, infrared, RF or other frequencies. When nothing is moving in the area, the bounced back signals are relatively uniform with slight variations due to temperature and air flow. However, when there is movement in the area that is being targeted, the echoed signals fluctuate. When the motion sensor detects fluctuations in the echoed signals, such as when the detected signals vary in spectrum, it is an indication that movement is occurring (i.e., someone is moving in bed).

In one embodiment, the area motion sensor is a passive infrared sensor (PIR sensor). In one embodiment, differential detection is used with the PIR sensor. Differential detection uses a paired set of sensor elements, such that the measurements cancel each other, to remove the average temperature in the field of view from the signal. This allows the sensor to avoid false indications of charge, and minimizes common-mode interference.

Figure 1B:
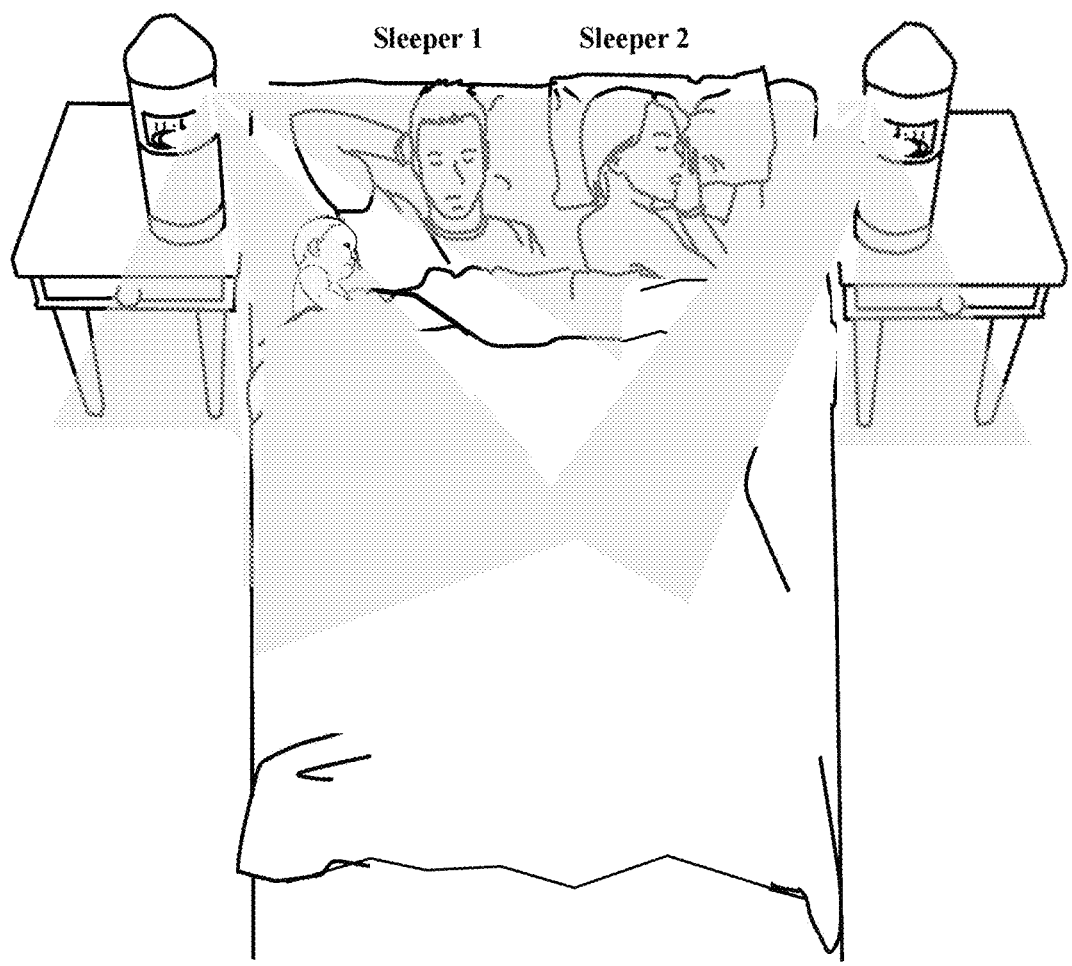
FIG. 1B is an illustration of an exemplary embodiment showing sleep tracking system for a sleep ecosystem.

In one embodiment, a sleep tracking device containing at least two area motion sensors detects the user's sleep state. FIG. 1B shows a sleep tracking device including two area motion sensors, one covering the bed area, and one covering the area next to the bed. Additionally, another person is shown as being in the sleep ecosystem, an infant. The sleep ecosystem, in one embodiment, may include areas outside the bed itself, if those areas are likely to impact the family members' sleep quality and waking patterns. For example, a pet on a pet bed may be part of the sleep ecosystem, because the movement of the pet would impact the sleep quality of the people in the bed. Therefore, in one embodiment, the sleep ecosystem may encompass an entire room, rather than only the bed. In such a case, the area motion sensors may encompass more of the room, or there may be more area motion sensors.

In one embodiment, the sleep tracking device may include additional sensors. The device may include, or receive data from sensors which can detect, in one embodiment, one or more of user movement, movement of other objects in the user's room, light levels, room temperature, air quality, oxygen level, carbon dioxide or other gas or particulate levels, user sleep state, humidity, sound, one or more user's body temperature, sleep cycles, and/or any data a sensor now known or developed in the future can detect. In one embodiment, based on the data from sensor(s), the sleep tracking system identifies the sleep state of the user(s) and determines the action or actions to be taken to adjust the sleeping environment of the user(s) to optimize the environment, help maintain and prolong the user's deep sleep status, improve the user's sleep duration and quality, and wake the user refreshed.

In one embodiment, various parameters the sleep ecosystem and environment are adjusted gradually and the effect on the users and the users' sleep cycle, quality, and duration is monitored. In one embodiment, the various parameters of two users' sleep environment is adjusted and monitored to determine the optimal environment for multiple users in the sleep ecosystem. These parameters may include temperature, light level, noise or noise cancelation, softness or hardness of the bed, sleeping and waking time, etc.

In some of the embodiments, the sleep tracking system monitors the effects and outcome of changing the environment, and based on the effect the adjustments have on each of the family members' sleep duration and quality, the sleep tracking system determines whether additional aspects of the one or more user's environment should be changed to provide an optimal environment and, through various changes in the user's environment and feedback on how those changes effected the user's sleep cycles, duration and quality, determines the optimal conditions for a user, more than one user or two or more users in the same environment or bed. In one embodiment, in addition to automatic feedback, the user may provide his or her personal feedback to the system as well.

In one embodiment, as shown in FIG. 1A, the sleep tracking device with multiple sensors can be used for a plurality of family members in the same bed or area. The sleep tracking device uses the multiple sensor areas, shown as Beams A, B, and C, to determine the motions of each user, and calculate the sleep data for each user based on that information. In one embodiment, the sensor areas are non-overlapping. In one embodiment, the users may have different preferences, and the system may be able to adjust preferences, such as temperature, sleep surface softness, sound and light levels, for each of the users. In one embodiment, the system may automatically detect the identity of the family member, and adjust the settings to their preferences.

In one embodiment, the sleep tracking system may include a plurality of sleep tracking devices. In one embodiment, this enables multiple users to have a separate sleep tracking devices. When multiple sleep tracking devices interact with each other, in one embodiment, they create a schedule and an environment that is most suitable for all of the users in the sleep ecosystem. For example, User A and User B each have a sleep tracking device. When A and B are in the same room or sharing the same bed, User A's sleep tracking device will interact with User B's sleep tracking device to create an optimal schedule and environment for both users. In one embodiment, if one of the users in the sleep ecosystem needs to wake up before someone else in the sleep ecosystem, the sleep tracking device will initiate a more gentle method (e.g., low level music, vibration, soft light) to wake User A so that User B will not be disturbed. If User A and User B enjoy different temperature and darkness, the sleep tracking device may further adjust the mattress to different temperatures and adjust lighting to have different levels of darkness in different areas. In one embodiment, when multiple sleep tracking devices are working together in a sleep tracking system, there are more sensors, and the accuracy of the system will increase. In one embodiment, the multiple sleep tracking devices can communicate with each other to determine the best parameters for the two people sleeping in the same environment, where the chosen parameters will be a combination/variation of the ideal parameters for each user.

FIG. 1B shows another sleep ecosystem including an infant. Unlike an adult, the infant would not sleep extending along the bed, from the head to the foot of the bed, but would generally be occupying a relatively small area. Despite their small size, infants have a large impact on the sleep experience of the adults sharing a bed with them. Therefore, the detection and identification of an infant is useful to set expectations and ensure that the users in the environment get the best sleep possible.

Figure 2:
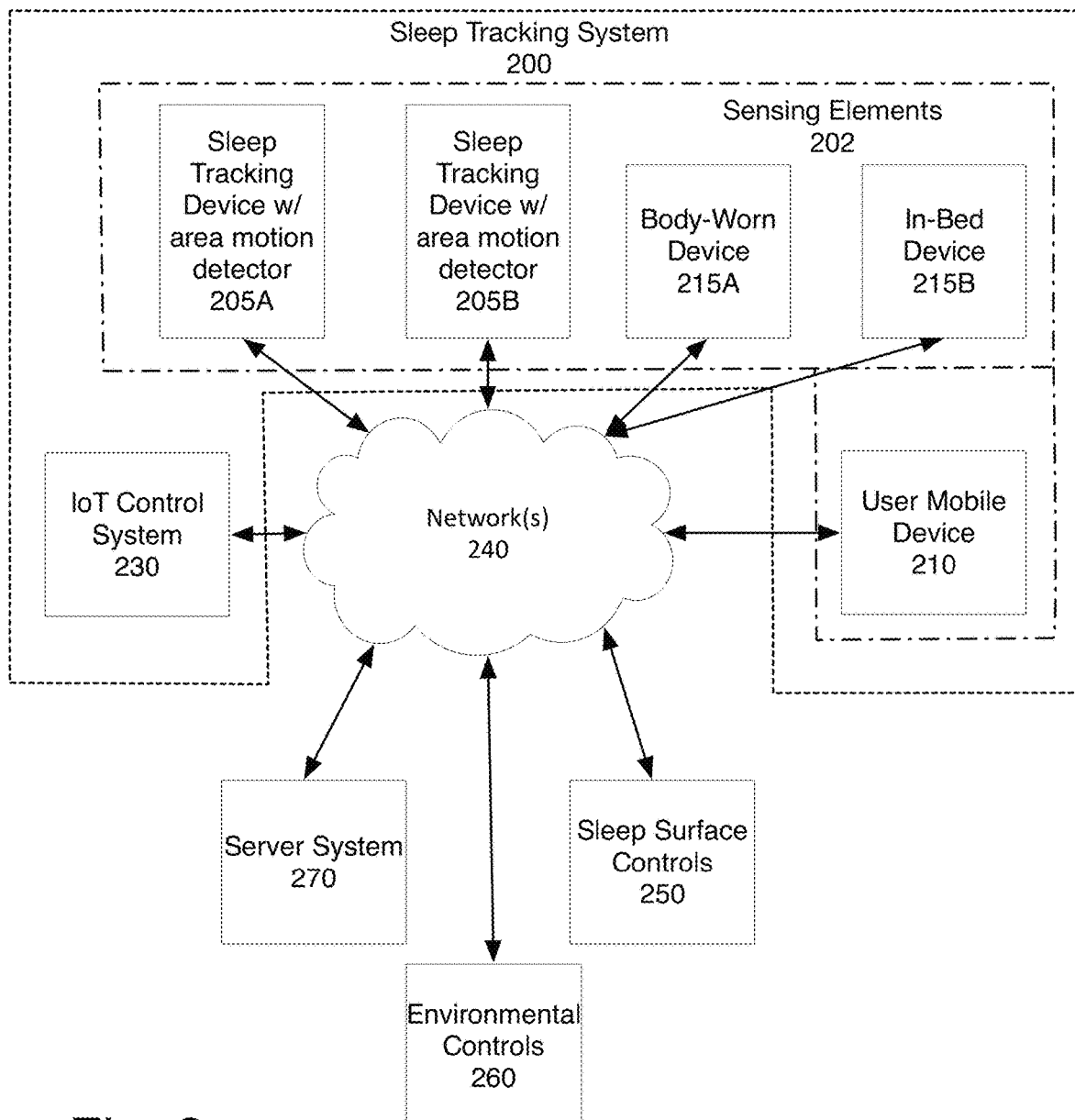
FIG. 2 is an exemplary diagram showing one embodiment of a sleep tracking system.

FIG. 2 is a system diagram showing one embodiment of the interactions between a plurality of elements in a sleep tracking system. Note that a single configuration need not include all of these elements. At a minimum the system should have a sensing element 202, whether area motion detector, body-worn device, or in-bed device. The combination of sensing elements may be used, but are not required. The user mobile device 210, in one embodiment, can act as a sensing element as well. The sleep tracking system 200 in one embodiment includes one or more sleep tracking devices, with area motion detectors 205A, 205B. In one embodiment, the system further may include a body-worn device 215A, and/or in-bed device 215B. A body-worn device 215A may be a wristband, watch, chest strap, headband or other device which is in contact with the user's body and include one or more sensors to sense the user's state. The in-bed device 215B may be an in-mattress/bedframe inductive sensor or accelerometer, a mattress topper, a pillow, or a blanket which includes one or more sensors to detect the user's state.

In one embodiment, the sleep tracking system interacts via wired or wireless network connections. In one embodiment, the mobile device 210 and the sleep tracking device 205A/205B interact via wireless connection (WiFi) or a local area connection such as a Bluetooth connection. while the mobile device interacts with the body-worn device or in-bed device 215A/215B, via a low power Bluetooth connection (BLE), or another type of connection. The body-worn device or in-bed device 215A/215B may interact with the sleep tracking device 205A/205B via BLE or Bluetooth connection as well. In some embodiments, the user's mobile device 210 may be plugged into the area motion detector 205A, which may provide a charging base for the mobile device 210. The connection between the area motion detector 205A/205B and the user mobile device may be a wired connection. Similarly, the in-bed device 215B may provide an element that can be connected via wires to the user mobile device 210.

This sleep tracking system 200 works together to provide information about the sleep ecosystem, including the sleep state of one or more family members in the sleep ecosystem, and to control the sleep environment. As noted above, the system need not include a body-worn device 215A/in-mattress device 215B or mobile device 210, but when such devices are available, the system may automatically connect to them and utilize the sensor data, or processing capability, available from them.

In one embodiment, the sleep tracking system may additionally include a wristband or similar body-worn device 215A including one or more sensors. These sensors may be used to track the user's movements directly, using an accelerometer, gyroscope, or similar sensor. In one embodiment, the body-worn device 215A may include sensors such as thermometers, to enable measurement of the user's body temperature. This can be useful for example, if the body-worn sensor detects that a user is experiencing a hot flash, the sleep tracking system can reduce the temperature of the room or the sleeping surface to improve the user's sleep cycle, keeping the user from waking up from the hot flash. In one embodiment, the sleep tracking system may control the body-worn device, to turn it, and or a subset of its sensors, on and off as needed. This reduces power use, since the body-worn device is battery dependent, but provides the additional sensor data when appropriate.

The sleep tracking system with the combined body-worn device 215A and table top sleep tracking device 205A/205B may include a variety of functions and monitoring features that enable the monitoring and tracking of the user's activity. In one embodiment, a body-worn device 215A and/or mobile device 210 can track movements of the user during the day for a variety of purposes, such as activity tracking, inactivity alerts, ergonomics, and other purposes. The body-worn device 215 or mobile device 210 can monitor the user's pulse, breathing rates, oxygen content, temperature, location, speed, etc., in one embodiment. Thus, such devices can be used for medical purposes, such as reporting suspect conditions. Further, such devices can be used for exercise or physical fitness purposes, such as monitoring intensity of workouts, calories burned, heart rates, etc. Such devices may also be used to track to the location of individuals, such as a wandering child, employees of a service or repair company, etc.

Thus, a single body-worn device 215A that may include multiple such functions may easily find a need for 24-7 usage thereby greatly limiting the down time for charging. Therefore, shutting off the body-worn device when it is not needed, extends the time between charging. In one embodiment, the sleep tracking system may include a docking station to receive the body-worn device 215 and/or mobile device 210, and allow the device to operate on a bedside table at night while being plugged in for charging. This allows the device(s) to be continually used during the day, while the sleep tracking system 200 monitors the user at night.

Any monitoring, body, sleep, sensor, band and communication, technology known to one of ordinary skill in the art, now or in the future, can be used in the sleep tracking system. The entire specifications from U.S. Pat. Nos. 7,647,195, 8,187,182 and 8,568,310 and U.S. application Ser. No. 13/622,325, filed on Sep. 18, 2012, U.S. Provisional Application No. 61/536,532, filed on Sep. 19, 2011, U.S. application Ser. No. 14/255,923, filed on Apr. 17, 2014, U.S.

Provisional Application No. 61/814,178, filed on Apr. 19, 2013, U.S. application Ser. No. 14/269,036, filed May 2, 2014, which include, among other things, various sensor, body, band, controlled sleep surface technologies, are hereby incorporated by reference in their entirety herein.

In one embodiment, the sleep tracking system 200 further includes a user mobile device 210. The user mobile device 210 may be a smart phone or similar device, in one embodiment including a sleep tracking or motion tracking application. In one embodiment, the user mobile device 210 may be used to control the sleep tracking device 205A, 205B, and provide more detailed output regarding the user's sleep quality and environment details, as well as enable the user to manually control the system and set preferences. In one embodiment, the user may also obtain detailed information about his or her sleep experience, and/or set preferences, via a webpage hosted on the server system 270, accessible through mobile device 210 or another computing device. In one embodiment, the sleep tracking devices may also include user interface elements, including optionally a touch screen, a browser, etc.

In one embodiment, the server system 270 receives data, via network 240 from sleep tracking system 200. The sleep tracking device 205A, 205B, or user mobile device 210 may provide network access, and provide data to the server system 270.

In one embodiment, the sleep tracking system 200 further includes Internet of Things (IoT) control system 230. The IoT control system 230 controls one or more aspects of a smart phone, including elements, such as a sleep control surface 250, or an environmental control 260, such as an air conditioning system or heating system, curtains, lights, air filter, or other environmental elements, which may be controlled via the sleep tracking system 200. IoT control system 230 may also control other home automation elements, such as door locks, lights outside the sleeping area, a coffee machine in the kitchen, etc. The sleep tracking system 200, in one embodiment, can control any relevant controls in the house which are available for control. In one embodiment, when the house has multiple sleep control systems 200 in different rooms, the sleep control systems 200 may work together to optimize IoT elements.

The sensors may be in a single sleep tracking device, and thus at the same location or in multiple devices at different locations. Additionally, the sleep tracking system 200 may include using more than one sleep tracking device 205A with multiple sensors that either act independently or work together. In one embodiment, two sleep tracking devices are provided, and each monitors one or more users in the room. The devices communicate with each other to determine both the ideal environmental and sleep parameters for the individual user and the ideal environmental and sleep parameters for both the users combined. The sleep tracking devices, and optionally other devices when available, together form the sleep tracking system 200. Based on data from a plurality of sensors, the sleep tracking system logically determines the sleep phase of the user and adjusts the sleeping environment accordingly. The sleep tracking system 200 may also control various elements of the sleep tracking system itself. For example, when the sleep tracking device detects that the user is sleeping, the sleep tracking system may place the user's body-worn device into sleep mode. As noted above, this may be a mode to monitor the user's sleep or a mode to shut of some or all of the body-worn device to reduce power consumption.

Figure 3:
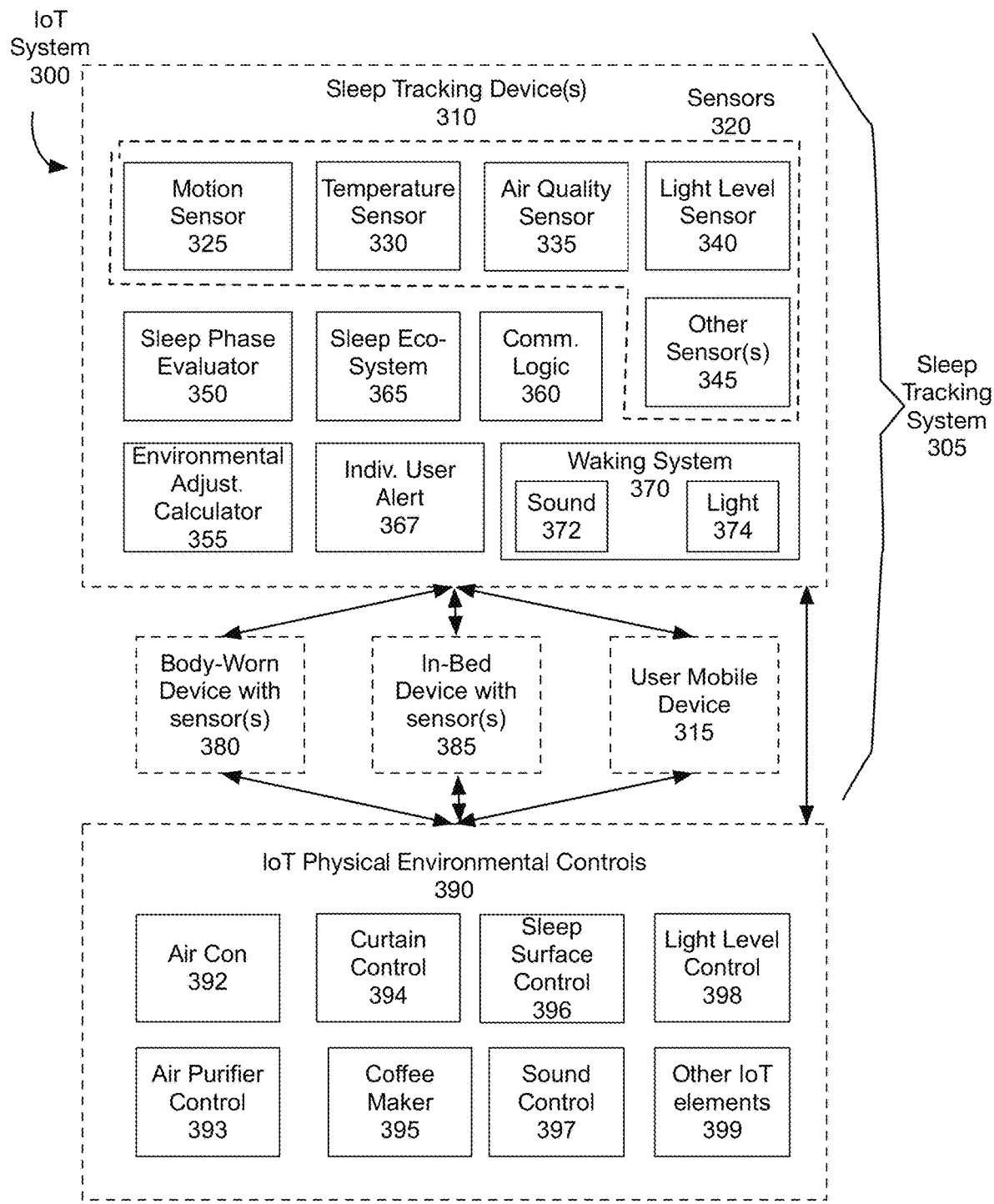
FIG. 3 is a block diagram showing aspects of at least one embodiment of the sleep tracking system.

FIG. 3 is a block diagram showing aspects of at least one embodiment of an Internet of Things (IoT) system 300, with the sleep tracking system 305. The sleep tracking system 305 includes one or more of a sleep tracking device 310, a user mobile device 315, a body-worn device with sensor(s) 380, and an in-bed device with sensor(s) 385. Sleep tracking device 310 may be a passive monitor, an inductive sensor, or another type of system. For simplicity, sensors and logics are only shown in the sleep tracking device 310, though is should be understood that a subset or superset of sensors and logics may be present in the body-worn device 380, in-bed device 385, and/or user mobile device 315.

The sensors 320 may include, for example, a motion sensor 325, temperature sensor 330, air quality sensor 335, light level sensor 340, and other sensors 345. In one embodiment, the motion sensor 325 is a passive sensor, such as a PIR sensor, in the sleep tracking device 310. In one embodiment, for the body-worn device 380 and/or in-bed device 385 the motion sensor 325 is an accelerometer or gyroscope to measure the user's movements. In one embodiment, the body-worn device 380 and/or in-bed device 385 may include a temperature sensor 330, to sense the user's body temperature. In one embodiment, the temperature sensor 330 may measure the user's body temperature as well as the room temperature.

In one embodiment, the air quality sensor 335 enables the sleep tracking system 310, in one embodiment, to monitor the user's bedroom's air quality to alert the user of unhealthy conditions and monitor correlations with sleep quality. In one embodiment, the air quality sensor 335 monitors for gases, such as carbon dioxide, carbon monoxide, radon, or other potentially toxic gases. The air quality sensor 335 monitors for particulate matter in the air.

In one embodiment, sleep ecosystem 365 identifies the family members who are in the sleep ecosystem. In one embodiment, without user input the system can automatically identify a human adult, human child, human infant, and pets, based on size, movement, and temperature, in one embodiment. In one embodiment, the system utilizes user input to further classify these identified types. In one embodiment, the system may automatically identify gender, as well as age category. In one embodiment, the system may be able to differentiate between cats and dogs, or other types of pets based on shape, movement, and temperature characteristics. In one embodiment, if the user provides input identifying the family members the determination may be specific (e.g. Joe whose characteristics may include gender, age, and any relevant health conditions) or general (e.g. age 40, adult male). In one embodiment, the system may use data input by the user via the user mobile device 315 to identify the family members who can be part of the sleep ecosystem. In one embodiment, the sleep ecosystem includes all adults, children, and pets that may be part of the environment. In one embodiment, the sleep tracking system 305 includes a plurality of sleep tracking devices 310, body worn devices 380, in-bed devices 385, and/or user mobile devices 315 to track users in multiple sleep zones.

In one embodiment, the sleep phase evaluator 350 determines the user's sleep phase for one or more of the family members, based on the data from the sensors. In one embodiment, the data from the various available sensors are integrated, to determine user temperature and movement, and other characteristics.

Environmental adjustment calculator 355 utilizes the data from the sleep phase evaluator 350 and sensors 320, to determine whether the system should adjust the user's environment. The environment may include physical environmental controls 390, and waking system 370. The system uses communication logic 360 to control the physical environmental controls 390, in one embodiment. The communication 360 may be part of one or more of the sleep tracking device 310, body-worn device 380, in-bed device 385, and/or user mobile device 315. In one embodiment, In one embodiment, the sleep tracking device 310 includes a sleep eco-system logic 365, to determine the presence and positions of the family members in the sleep eco-system. The use of a sleep ecosystem enables the system to adjust its recommendations and settings based on the needs of everyone s in the sleep ecosystem.

In one embodiment, the sleep tracking system may include a body-worn device 380, such as a wristwatch or bracelet, arm band, headband, or other device. Such embodiments may include an internal charger and an interface for receiving an external power source. Such embodiments may thus be worn by a user while awake and while sleeping or, may be removed during sleeping and plugged into a power source for charging.

In one embodiment, the sleep tracking device 310 may include a docking station for a mobile device 315 and/or a body-worn device 380. In such embodiments, the docking station may receive the device(s) and once coupled together, operate as a charging station for the device. For example, the mobile device 315, and/or a body-worn device 380 may include sensors to detect motion, such as accelerometers, as well as any of the previously mentioned detection and tracking capabilities. When the user is going to sleep, the device can be connected to the docking station for charging. The sleep tracking device including the docking station can then use its own hardware and/or software, the hardware and/or software of the device or, a combination of both, to track the user's sleep while the user mobile device 315 or body-worn device 380 is charged.

Waking system 370 controls sound 372 and light 374, in one embodiment, provided by sleep tracking device 310. In one embodiment, the system adjusts the lighting and sound to help the user fall asleep, stay in the right sleep state, and wake up. The waking system 370 may include other elements, such as vibration or scents, in one embodiment. In one embodiment, other environmental controls may also be controlled by the waking system 370. For example, in one embodiment, the waking system 370 may control the IoT in the house, to set the physical environmental controls 390 to start the user's coffee machine, when the user is starting to wake, to trigger the coffee smell as well as to provide fresh coffee to the user when he or she gets up. The waking system 370 may also send a signal to curtain control 394 to open the blinds or curtains, to provide natural light, or close them to help the user fall asleep.

The sensor data may be used to continually monitor the user's sleep state and, when it is determined from the signals that the user has entered a stage of light sleep, the alarm time may be compared with the timing of the light stage of sleep—the "timing" of the sleep stage being a beginning time, an ending time and the period of time defined between. If the alarm time coincides with the timing of the entered stage of light sleep, an alarm or stimulus can be triggered to wake the user. The stimulus could be any of a variety of actions such as audible alarm, music, vibration, light, temperature fluctuations, other sounds, etc. In some embodiments, a gradually intensifying stimulus of light can be made to simulate a dawn event of the sun rising, gradually increasing noise, gradually decreasing white noise, etc.

In one embodiment, the light 374 is a smart reading light, which utilizes the information about when the user is falling asleep and initiates a lighting sequence that helps the user fall asleep faster when they choose to. Similarly, the sound 372 may select appropriate music and/or sound selections to create a calming and relaxed ambience for falling asleep faster. The light 374 and sound 372, and other environmental controls 390 may also be used to ensure that the family members in the sleep ecosystem stay in the optimal sleep phase.

In one embodiment, the system turns off the light 374, when it determines the family member(s) are starting to fall asleep. In one embodiment, the sleep tracking device 310 may also provide a night light, which is available when the system determines the user has woken, and is likely to get out of bed, for example to go to the bathroom. In one embodiment, the light 374 also provides a reading light, which automatically turns off when the user falls asleep.

In one embodiment, the light 374 also may be used to guide the user to wakefulness, using a dawn-type lighting progression. In one embodiment, the light 374 may be a multi-color light, such as a multi-colored LED, and the color tones may be selected to assist in waking and/or falling asleep. For example, the human body and brain is adapted to recognize the colors associated with the sun rising with wakefulness. Similarly, a user falls asleep more easily having been exposed to blue-toned lights rather than yellow toned lights, before falling asleep. Therefore, the light 374 may set the color/tone of the light to assist in the user's sleep and waking states.

In one embodiment, the speakers, lights or other sound or light emitting components of the sleep tracker device are arranged vertically to give the user the illusion or sensation of sound and/or light moving up and or around the room (e.g. waking up to the sun rising or noises that seem to get closer and/or farther from the user that gradually increase in volume).

In one embodiment, the user can set an alarm time, representing a desired time to wake up, in a personal device such as the user mobile device 315, or on the sleep tracking device 310. In one embodiment, the system uses a master sleep cycle curve, mapping the user's movement through the stages of sleep, that is updated with data collected from the monitored signals and then analyzed to predict an upcoming stage of light sleep that the user may enter. Subsequently, an alarm time is compared to the predicted timing of the upcoming stage of light sleep and, if the alarm time coincides with the timing of the upcoming stage of light sleep, a start time is calculated for triggering an alarm to awaken the user. At the start time, an alarm comprising stimulus to awaken the user coincidentally with his entering the upcoming stage of light sleep.

In one embodiment, in addition to a user input alarm time, the sleep tracking system may synchronize with the users calendar in a the user's smart phone 315, on the cloud or otherwise accessible, and include information about the user, such as location, commute to meeting, desired leisure time, preparation time, etc., and then heuristically derive an optimal awakening time or window that would allow time for the user to accomplish the user's schedule. The alarm time represents a desired time that the user wishes to wake up, and is adjusted to a time when the system should start rousing the user, so that the user can be sure to be awake at the alarm time. In one embodiment, because the average sleep cycle is 90 minutes, the user may set the "waking time" as a window, rather than a particular time, e.g. within 30 minutes of 7:30 a.m.

Other IoT systems may optionally be controllable by sleep tracking system, via sleep tracking device 310, user mobile device 315, or in-bed device 385. The physical environmental controls may include air conditioning 393, curtain controls to open and close curtains 394, sleep surface control 396 to alter the temperature and/or firmness of the sleeping surface, light level control 398 to alter the light level in the room (turn off, dim or brighten the light in the room), air purifier control 393, and sound control 399 to control external speakers and/or radio/music/sound players. Additionally, the sleep tracking system 310 may interface with any other elements that can be controlled over an IoT network, such as a door lock, coffee maker, teapot, remote start for a vehicle, etc. For example, if the user lives in an area where it is very cold, the system may start a heat lamp in the bathroom, or start heating the car's engine. Of course, such systems may be controlled in relationship to waking, and thus may be initiated prior to, concurrently with, or after the user wakes up.

Figure 4:
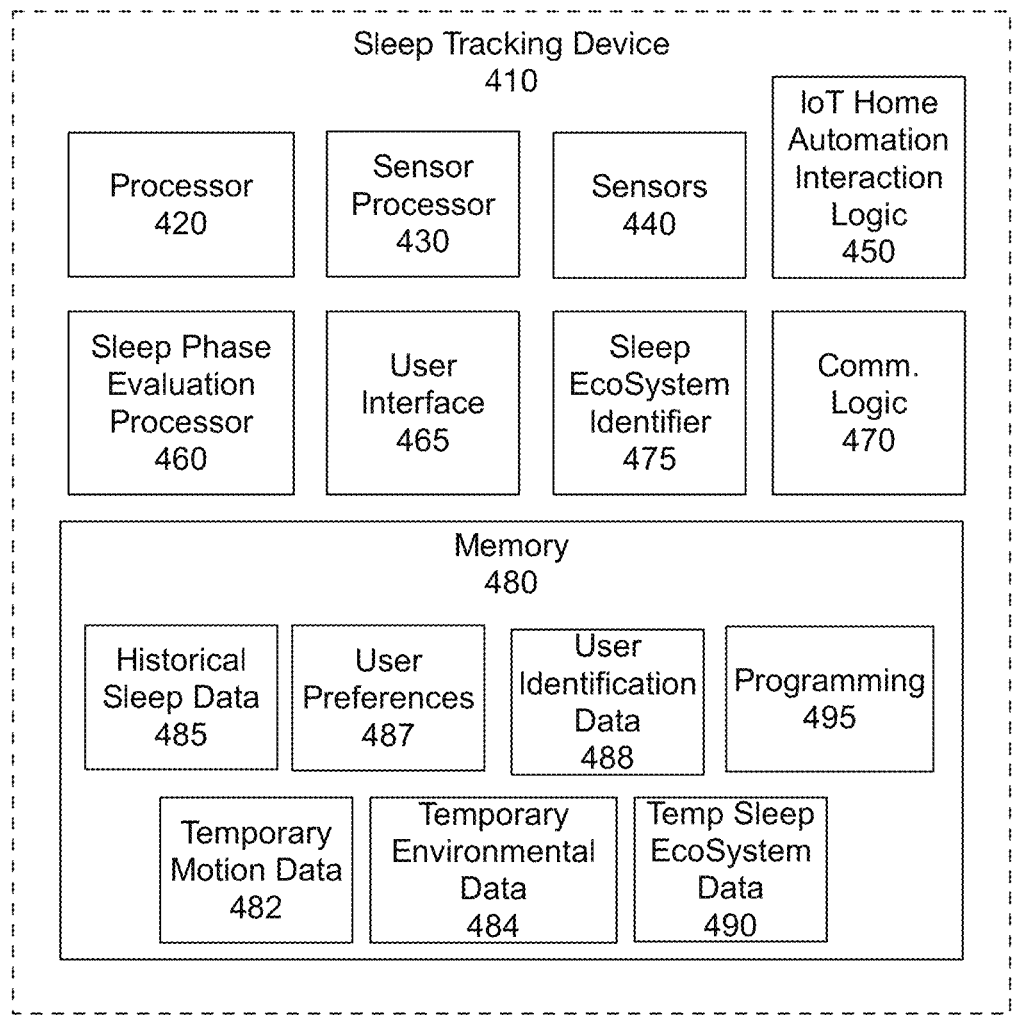
FIG. 4 is a block diagram showing elements of one embodiment of a sleep tracking device.

FIG. 4 is a block diagram showing elements of one embodiment of the sleep tracking device. The sleep tracking device 410 includes in one embodiment, a primary processor 420, a sensor processor 430, and a sleep phase evaluation processor 460. In another embodiment, device may include a single processor, more or fewer processors. The processors 420, 430, 460 may be a central processing unit (CPU), a digital signal processor (DSP), or another type of processing system.

The sensors 440 in one embodiment may include the area motion sensor, temperature sensor, light sensor, and other sensors. The system also may include communication logic 470, which in one embodiment, enables the sleep tracking device 410 to communication with outside systems. The system in one embodiment further includes a user interface 465 which enables the user to interact with the sleep tracking device 410. In one embodiment, the user interface 465 may be as simple as an alarm clock or light switch. In one embodiment, the user interface 465 may be as complex as keyboard or touch screen and LCD to receive input and/or provide output to the user. In one embodiment, in addition to a simple user interface on the sleep tracking device 410, the user may obtain more complex data via a device that communicates with the sleep tracking device via communication logic 470.

Sleep ecosystem identifier 475 processes the sensor data from a plurality of sensors and available information to determine which family members are part of the sleep ecosystem. This is used to optimize the sleep environment for the current population of the sleep ecosystem, enabling adjustment for various impacts of additional persons or animals in the environment.

In one embodiment, the memory 480 stores temporary motion data 482, temporary environmental data 484, and temporary sleep ecosystem data 490, to enable the processors to use the data in predicting and analyzing the data. In one embodiment, memory 480 also stores data obtained from other devices, such as in-bed devices, body-worn devices, or mobile devices, which may be integrated with the data obtained by the sensors of the sleep tracking device 410. This integrated data set may be used by the processors to identify the sleep ecosystem, and users' sleep phase.

In one embodiment, memory 480 includes historical sleep data 485, user preferences 487, programming 495, user identification data 488, and contextual settings 490. Contextual settings 490 are the preferred settings for the user, based on the historical data and user input. User identification data 488 provides the information about the family members that may be part of the sleep ecosystem. As noted above, this may be automatically derived data (e.g. adult/ child/animal) or correlated data based on user input, either directly into the sleep tracking device 410 or via an external device such as a mobile device. In one embodiment, the sleep tracking device 410 may include a camera, and the family members may be in part identified based on camera/ video data.

In one embodiment, memory 480 may be a flash memory, or another type of non-volatile memory. Other forms of data storage, including ROM (read-only memory) may be used for some portions of memory 480. Although memory 480 is illustrated as one block, it should be understood that memory may be distributed in various ways, and may include multiple types of memory. For example, temporary motion data 482 may be stored in a cache associated with sensor processor 430, while programming data 495 may be stored in a read-only memory, or other memory, associated with the main processor, or independent from it. In one embodiment, the programming 495, as well as contextual settings 490 may be updated from a server system (not shown). In one embodiment, the historical sleep data 485 may also be shared with the server system.

Figure 5:
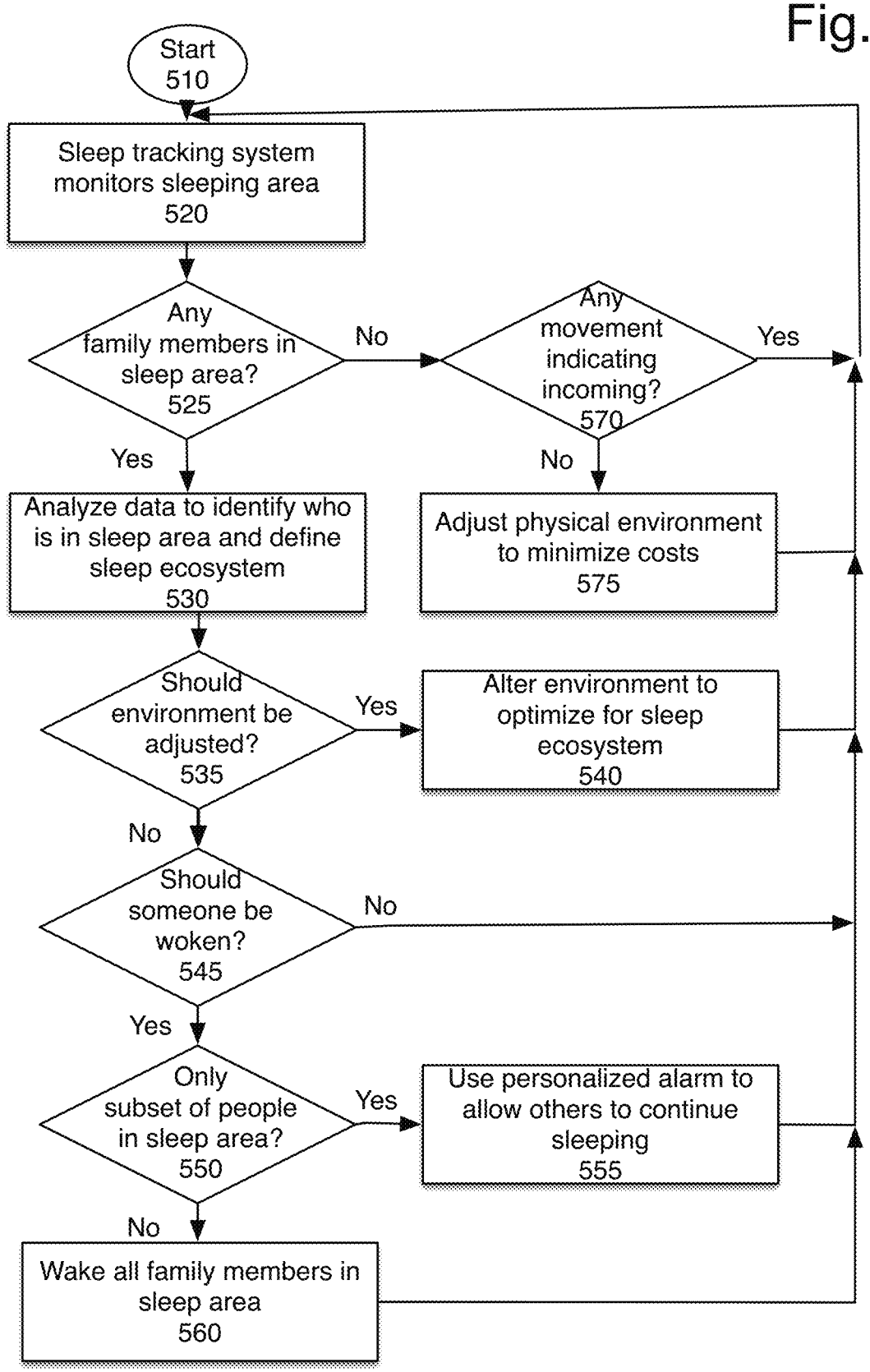
FIG. 5 is a flowchart of one embodiment of monitoring and controlling the sleep ecosystem.

FIG. 5 is a flowchart of one embodiment of monitoring the sleep ecosystem using a sleep tracker or other device. The process starts at block 510. The process, at block 520, monitors the sleeping area that defines the sleep ecosystem. In one embodiment, this may be a bed. In another embodiment, this may include an entire room, or even larger space. The monitoring may use a combination of one or more sleep tracking devices, in-bed sensors, mobile devices, or body-worn devices.

At block 525, the process determines whether there are any family members in the sleep area. In one embodiment, this monitoring uses motion data. If no family members were detected in the sleep area, the process determines whether there is movement indicating that a family member is about to enter the sleep area. If not, the process returns to block 520 to continue monitoring the sleeping area. In one embodiment, at block 575 the system adjust the physical environment for the absence of users. In one embodiment, this may include opening or closing the blinds, turning off lights, adjusting temperatures, etc. In one embodiment, this adjustment may be targeted to minimizing costs, e.g. heating or cooling costs. The process then continues to block 520, where the system continues to monitor the sleeping area. If some potential movement is detected, the process continues to block 520, to continue monitoring until a family member is identified as being in the sleep area.

If there are family members in the sleep area, the process continues to block 530. At block 530, the system analyzes the movement and other available data to identify which family member(s) are in the sleep area, and define the sleep ecosystem. The sleep ecosystem includes the family members in the sleep area, as well as environmental conditions, in one embodiment. In one embodiment, if the prior state included some family members, but the addition is a new family member added to the sleep ecosystem the sleep ecosystem is updated, with the new data.

If there is at least one family member in the sleep area, the process at block 535 determines whether the environment should be adjusted. The environment is adjusted based on the identity of the family members in the sleep area. In one embodiment, the environment may further be adjusted based on the known sleep schedules of the particular family members. For example, if a child takes an afternoon nap, the environment would be differently adjusted then if a cat came into the bedroom in the afternoon. In one embodiment, the system calculates the intended sleep schedule of each member of the family based on historical data. Any user can then override this intended schedule.

At block 540, the system alters the environment if appropriate to optimize the sleep ecosystem for the intended use. The process then returns to block 520, to continue monitoring.

If the environment does not need adjustment, at block 545, the process determines whether someone should be woken. If not, the process returns to block 520 to continue monitoring.

If someone needs to be woken, at block 550 the process determines whether everyone in the sleep ecosystem should be woken. If so, all family members in the sleep area are woken, at block 560. In one embodiment, this my be done by gradually increasing light levels or sounds, or other methods. If only a subset of people should be woken, at block 555 a personalized alarm is used for the individual users who should be woken. In one embodiment, a personalized alarm may be a low sound, a directed sound to the particular user, a directed light, or some other interaction targeted to the user. In one embodiment, the personalized alarm may be a vibration or other notice using a body-worn system of the user. The process then returns to block 520, and continues monitoring. In one embodiment, alarms get progressively louder, stronger, or more insistent, as needed.

One of ordinary skill in the art will recognize that the process is a conceptual representation of the operations used to monitor the a sleep ecosystem and optimize it for the family members that are in the sleep area. The specific operations of the process may not be performed in the order shown and described. The specific operations may not be performed in one continuous series of operations, and different specific operations may be performed in different embodiments. Furthermore, the process could be implemented using several sub-processes, or as part of a larger macro process. Additionally, the description focuses on waking a user, however a similar process may be utilized for assisting a user in falling asleep. Furthermore, though this is illustrated as a flowchart the various logic blocks described may be triggered by interrupt or other processes, and need not include all blocks shown, or in the order shown.

Figure 6:
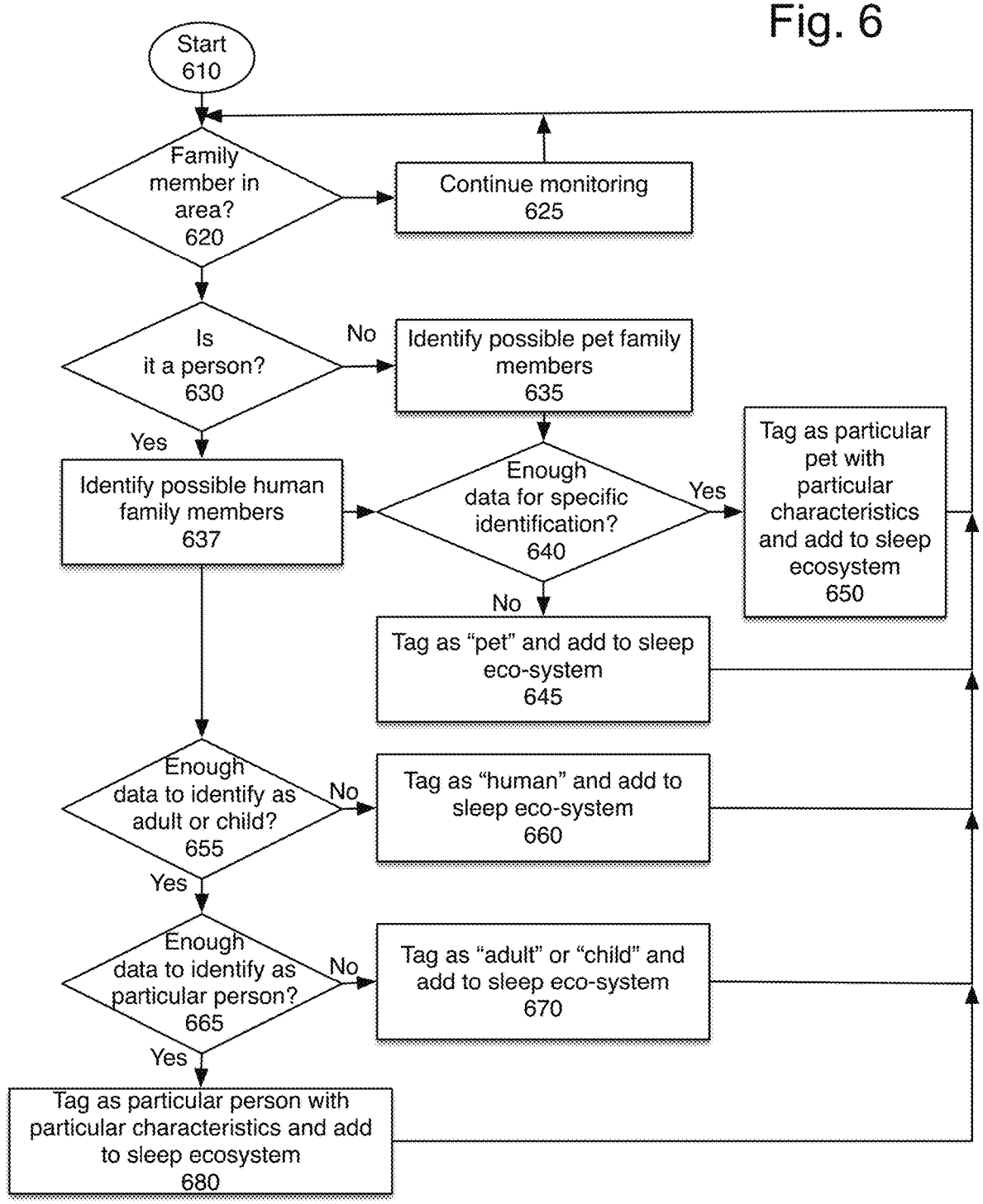
FIG. 6 is a flowchart of one embodiment of identifying the family members in the sleep ecosystem.

FIG. 6 is a flowchart of one embodiment of identifying the family members in the sleep ecosystem. The process starts at block 610. In one embodiment, the process starts when a family member enters the area defining the sleep ecosystem, as determined at block 620. If there is no family member in the area, the process continues to monitor, at block 625. In one embodiment, as discussed above, the environment may be adjusted for emptiness, for example by turning off lights, closing blinds, lowering heat, etc.

If there is a family member in the area, at block 630, the process determines whether it is a person. As noted above, family members can include humans as well as animals. If it is not a person, at block 635, the system attempts to identify the possible pet family members. In general, the system is more efficient if the user provides a list of possible family members. However, even without that list the system can utilize the movement data to make an educated guess about the identity of any family member.

At block 640, the process determines whether there is enough data for specific identification. There may be enough data if the movement data conclusively shows a particular pet. For example, if the household owns one cat and one dog, it is very likely that a pet that leaps up onto a bookshelf in the bedroom is a cat. Similarly, certain types of movements are fairly unique to dogs. If there is enough data, at block 650 the pet is tagged with the relevant particulars, and added to the sleep ecosystem.

If there is not enough data, the tag is simply "pet," and the pet is added to the sleep eco-system. The process then returns to block 620 to continue monitoring the sleep ecosystem.

If, at block 630 the process determined that the family member was human, the process at block 637 identifies possible human family members. At block 655, the process determines whether there is enough data to identify the family member as a child or adult. Generally, children are smaller and move more rapidly than adults. If there is not enough data for a child v. adult tag, the family member is tagged as a human and added to the sleep ecosystem. The process returns to block 620, after tagging the family member.

If there is enough data to identify whether the family member is a child or an adult, at block 665, the process determines whether there is enough data to identify the family member as a particular person. A particular person need not be a named individual. Rather, it is a uniquely identified person from among the family members. It may be "40 year old male" or "tall man," as long as the identification is unique within the family, that is sufficient.

If there is enough information for unique tagging, that is applied, at block 680. Otherwise, the person is tagged as an adult or child member of the family. In this way, each of the people in the sleep ecosystem is identified. Once this type of identification is done, the system can then adjust the sleep ecosystem to optimize for the family members currently in the sleep ecosystem.

As should be obvious, the more information about the particular people in the sleep ecosystem is made available to the system, the more accurate the system is in evaluating sleep quality, adjusting the environment, and ensuring that each person is woken up appropriately. However, even with the very limited amount of data the system can deduce based on sensor data, the sleep ecosystem approach improves the overall experience.

One of ordinary skill in the art will recognize that the process is a conceptual representation of identifying family members. The specific operations of the process may not be performed in the order shown and described. The specific operations may not be performed in one continuous series of operations, and different specific operations may be performed in different embodiments. Furthermore, the process could be implemented using several sub-processes, or as part of a larger macro process.

Figure 7:
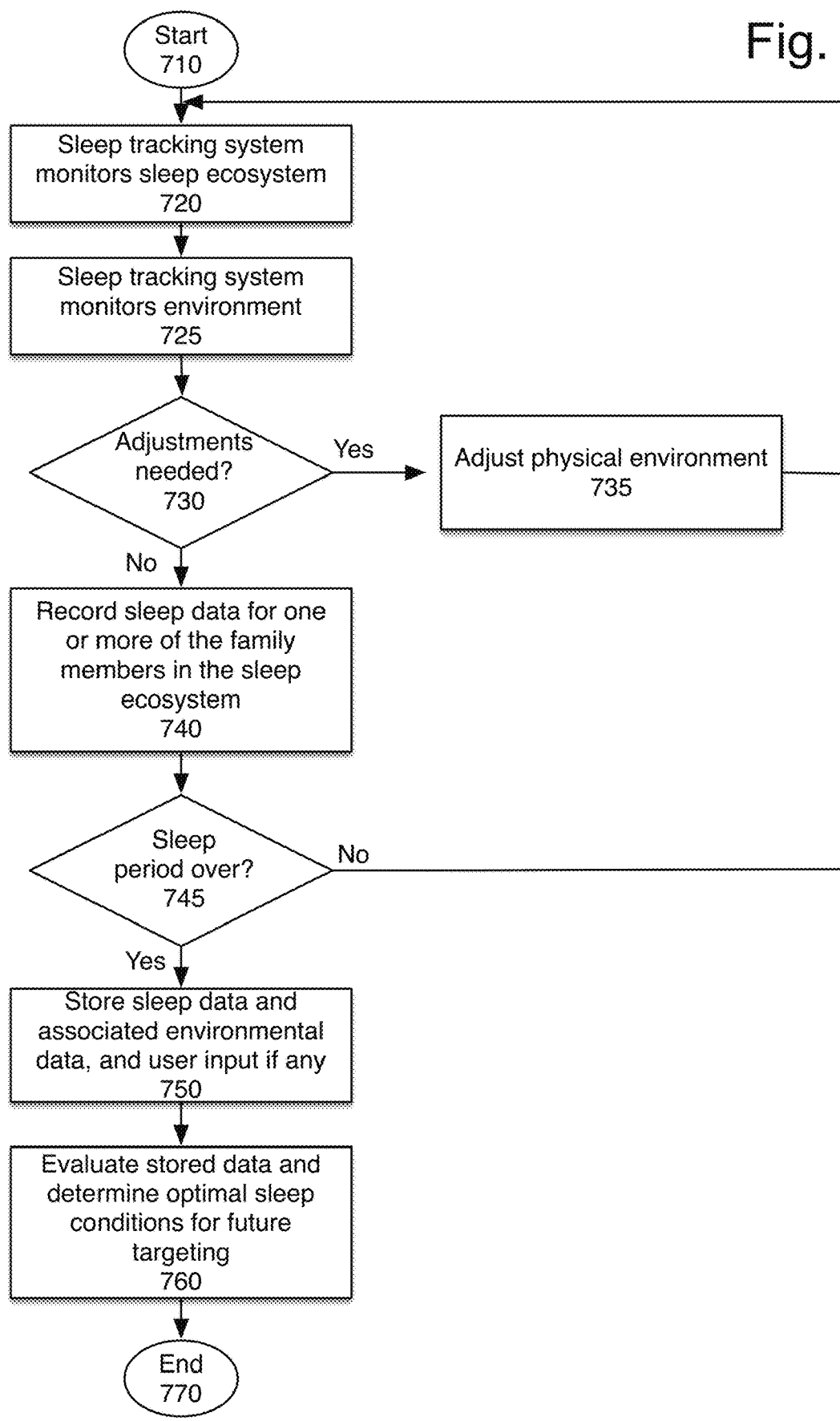
FIG. 7 is a flowchart of one embodiment of using the sleep tracking system to optimize the user's environment.

FIG. 7 is a flowchart of one embodiment of using the sleep tracking system to optimize the environment for the sleep ecosystem and the family members in the sleep ecosystem. The process starts at block 710. At block 720, the sleep tracking system monitors the sleep ecosystem. At block 725, the sleep tracking system monitors the user's environment.

At block 730, the process determines whether any adjustments are needed. The sleep tracking system can take actions to maximize the sleep quality of the family members in the sleep ecosystem. For example, when the sensors detect that User 1 of FIG. 1A or 1B is approaching the bed around 11:30 pm and has not left the bed in the following few minutes, the sleep tracking device will conclude that User 1 is in the process of going to sleep. The sleep tracking device will turn the light off (either instantly or gradually) and/or start a pre-selected music or white noise to assist sleep. In one embodiment, the change in the pattern of movement from reading in bed, or going to sleep, and falling asleep is detected. Action initiated by the sleep tracking device can be customized based on the user's preferences. In one embodiment, the user can override the actions using a user interface. In one embodiment, the user interface may be a verbal command, e.g. "I'm reading," or "lights on."

Once the user is determined to have fallen asleep, the sleep tracking device may turn off the music and/or start lowering the temperature of the mattress or room to maximize the user's sleep quality.

However, for example, if User 1 is already asleep, and User 2 joins the sleep ecosystem, the sounds selected may differ, to ensure that User 1's sleep is not interrupted. In one embodiment, other environmental adjustments may be made based on the family members in the seep ecosystem. For example, the overall temperature may be lowered if a pet is sleeping across the feet of the humans. As another example, when an infant is in the bed, the room temperature may be raised since young children are generally more sensitive to cold while asleep.

In one embodiment, the sensors used by the sleep tracking system are not limited to area motion sensors. The sleep tracking system may further include be temperature sensors, light sensors (such as photodiodes), air quality sensors, etc. Thus, the sleep tracking device can also monitor environmental conditions, such as the temperature of the room, sleepers, and mattress, brightness of the room, and the quality of the air (e.g., carbon dioxide or oxygen levels, particulates, allergens, CO2/Radon or other pollutants). In one embodiment, the sleep tracking system may also be able to make adjustments to other local conditions and aspects of the user's home.

If no adjustments are needed, the sleep data is recorded, at block 740 for one or more of the family members. In one embodiment, only human sleep patterns are recorded and measured. In another embodiment, the system may record the sleep data of the animals. Such sleep data may be found useful by the pet owners.

At block 745, the process determines whether the sleep period is over. If not, the process returns to block 720 to continue monitoring the sleep ecosystem.

If the sleep period is over, the sleep data is recorded, at block 750. The sleep data recorded may include details about the sleep ecosystem, relevant environmental data, control information as well as local data.

In one embodiment, each person in the sleep ecosystem may optionally provide information regarding the quality of sleep, level of tiredness and/or perception of sleep patterns, quality, or duration. In one embodiment, the users may also provide other data, for integration with the system. This data is also recorded, at block 750. The device takes that information into consideration when determining the ideal conditions and environmental and sleep parameters for the users or the sleep ecosystem in which the users are. For example, the user can indicate that he or she is more tired than usual. The sleep tracking device can take this information into consideration when determining the user's optimal sleep parameters, and recommended sleep patterns for subsequent days.

At block 760, the system evaluates the stored data, and determines the optimal sleep conditions for future targeting. In one embodiment, the sleep tracking device monitors the user's sleep throughout the night and adjusts the user's environment to ensure that the user has an optimal sleep experience. In one embodiment, the adjustment may include adjusting the temperature of the sleeping surface and/or room. For example, if the sleep tracking device predicts that the user is about to get up and leave the bed (i.e., to use the restroom), the sleep tracking device may adjust the temperature of the room or mattress beforehand so that the user will not feel great discomfort when leaving the bed, which typically will allow the user to fall back sleep quicker afterwards and result in a better sleep.

One of ordinary skill in the art will recognize that the process is a conceptual representation of the operations to use the sleep tracking system to optimize the user's environment. The specific operations of the process may not be performed in the exact order shown and described. The specific operations may not be performed in one continuous series of operations, and different specific operations may be performed in different embodiments. Furthermore, the process could be implemented using several sub-processes, or as part of a larger macro process.

As used in this description, the terms "component," "database," "module," "system," "processing component" and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component. One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet or local Wi-Fi with other systems by way of the signal).

Aspects, features and advantages of several exemplary embodiments of the present disclosure will become better understood with regard to the following description in connection with the accompanying drawing(s). It should be apparent to those skilled in the art that the described embodiments of the present disclosure provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated and equivalents thereto. Hence, use of absolute terms such as, for example, "will," "will not," "shall," "shall not," "must" and "must not" are not meant to limit the scope of the present invention as the embodiments disclosed herein are merely exemplary.

In this description, the terms "phase," "sleep phase" and "sleep period" are used interchangeably to represent a block of time, from sleep entry to awakening, during which a person sleeps. The terms "stage," "sleep stage," "light stage" and "deep stage" are used to describe smaller spans of time within a larger "sleep period" that may combine in various combinations to form one or more "sleep cycles." As such, one of ordinary skill in the art will recognize that multiple "sleep stages" may be combined to form a "sleep cycle" and multiple "sleep cycles" may be combined to form a "sleep period."

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed. It should be appreciated that the present invention could be performed on a device such as a computer or any device having a processor and memory or on a computer readable medium to be used on or executed by a computer. The term "content" may also include files having executable content, such as: object code, scripts, byte code, markup language files, and patches. In addition, "content," as referred to herein, may also include files that are not executable in nature, such as documents that may need to be opened or other data files that need to be accessed.

Figure 8:
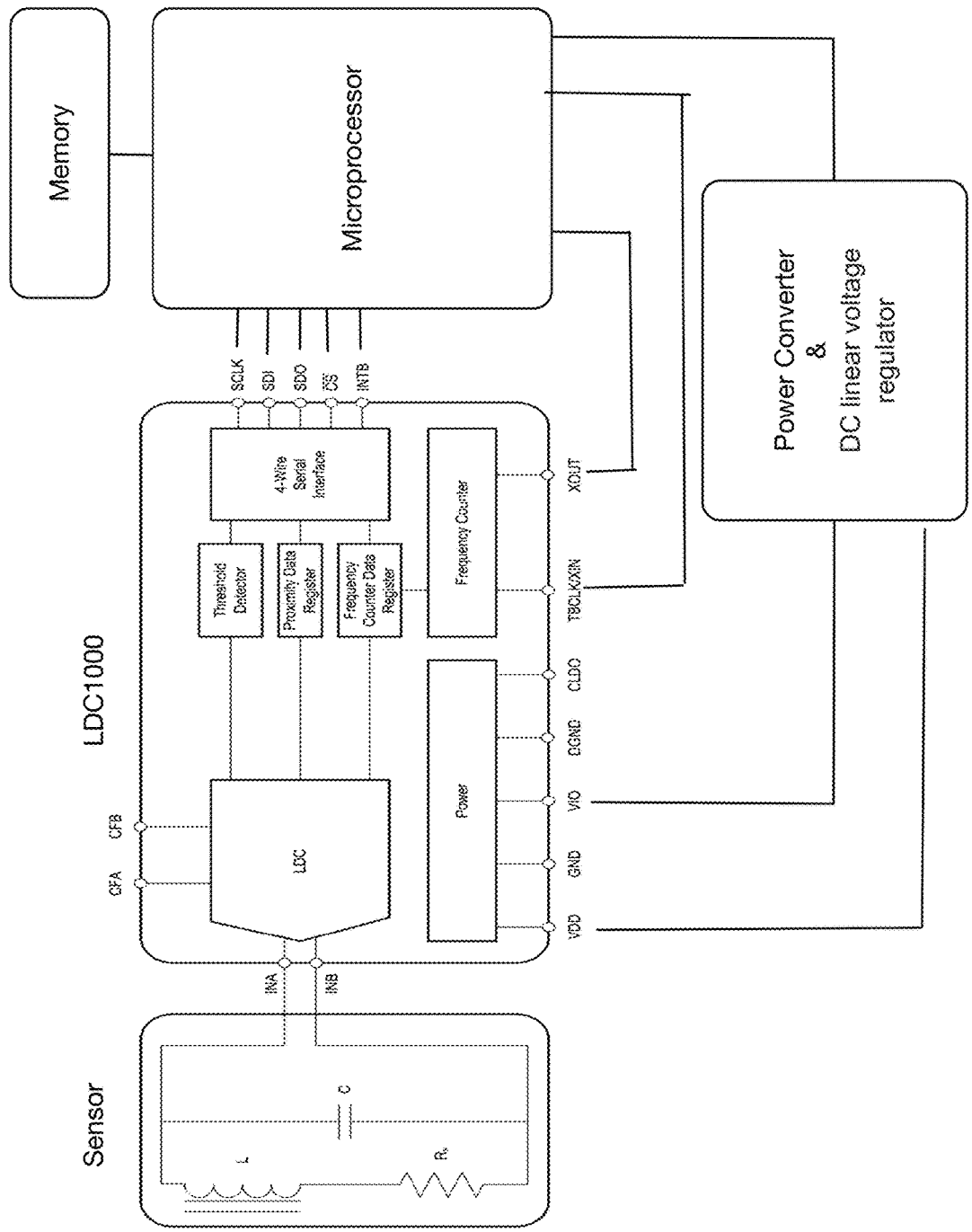
FIG. 8 is a diagram of one embodiment of an inductive sensor system that may be used with the present invention.

FIG. 8 is a diagram of one embodiment of the inductive sensor which may be used in the present invention, as part of an in-bed device. As noted above, an inductive sensor may be built into the mattress, box spring, bed frame, or other part of the user's bed. In one embodiment, it may be placed between the mattress and box spring or bed frame, rather than built in. The system is designed to provide a high sensitivity motion sensor, which in one embodiment is capable of identifying heart beats, breaths, as well as micro-motions, and use this data not only to identify all family members in the sleep ecosystem, but also to monitor each family member. This data can then be used to optimize the user experience.

The sensor, in one embodiment, receives power from circuit LDC1000, and sends signal data back to LDC1000. The LDC1000 is coupled to a microprocessor, which includes either on-board or coupled memory to store data. Power converter provides power to LDC1000. In one embodiment, the power converter provides low power AC to the sensor as well as DC power to the microprocessor and circuit LDC1000. In one embodiment, the sensor and LDC1000 are placed into the box spring or mattress, while the microprocessor and power converter are coupled via a cable such as a CAT5 cable. In one embodiment, microprocessor, memory, and power converter are plugged into the wall, and provide processing of the data. In one embodiment, microprocessor may include a network connectivity capability. Alternatively, the network connection may be external to the microprocessor, but part of the sensor system.

Figure 9:
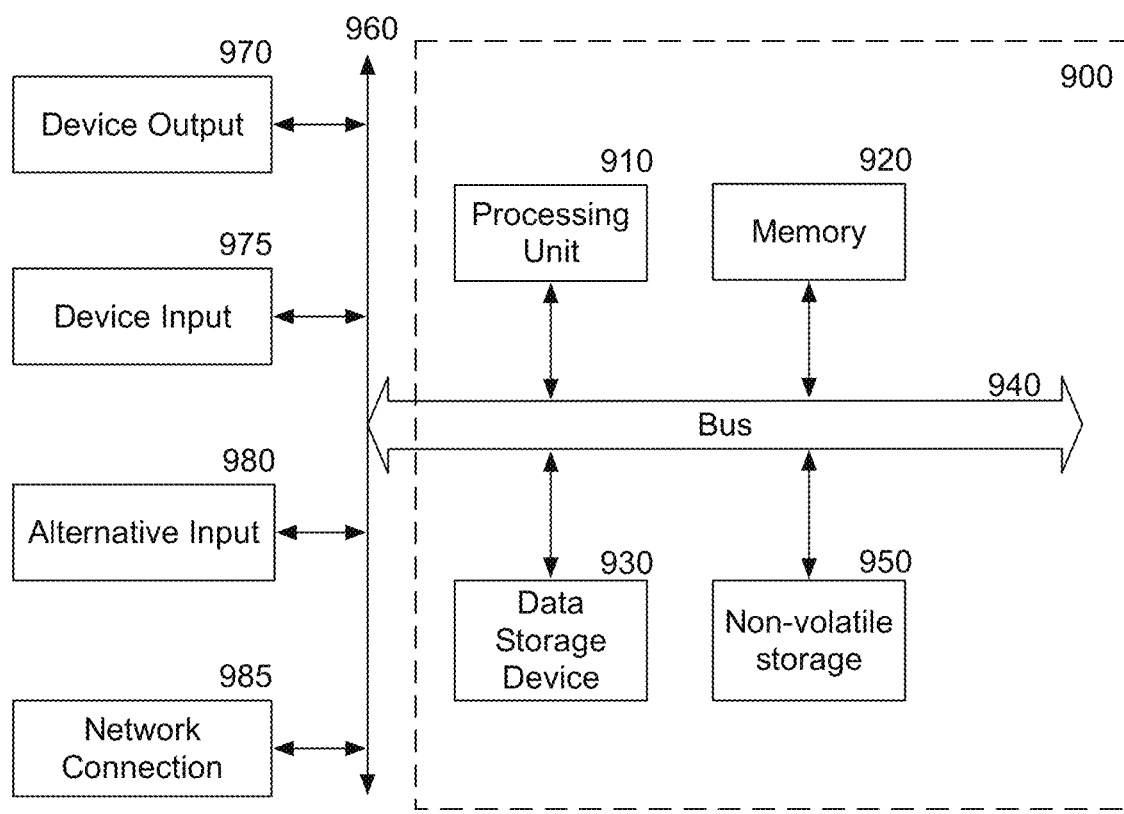
FIG. 9 is a block diagram of one embodiment of a computer system that may be used with the present invention.

FIG. 9 is a block diagram of one embodiment of a computer system that may be used with the present invention. It will be apparent to those of ordinary skill in the art, however that other alternative systems of various system architectures may also be used.

The data processing system illustrated in FIG. 9 includes a bus or other internal communication means 940 for communicating information, and a processing unit 910 coupled to the bus 940 for processing information. The processing unit 910 may be a central processing unit (CPU), a digital signal processor (DSP), or another type of processing unit 910.

The system further includes, in one embodiment, a random access memory (RAM) or other volatile storage device 920 (referred to as memory), coupled to bus 940 for storing information and instructions to be executed by processor 910. Main memory 920 may also be used for storing temporary variables or other intermediate information during execution of instructions by processing unit 910.

The system also comprises in one embodiment a read only memory (ROM) 950 and/or static storage device 950 coupled to bus 940 for storing static information and instructions for processor 910. In one embodiment, the system also includes a data storage device 930 such as a magnetic disk or optical disk and its corresponding disk drive, or Flash memory or other storage which is capable of storing data when no power is supplied to the system. Data storage device 930 in one embodiment is coupled to bus 940 for storing information and instructions.

The system may further be coupled to an output device 970, such as a cathode ray tube (CRT) or a liquid crystal display (LCD) coupled to bus 940 through bus 960 for outputting information. The output device 970 may be a visual output device, an audio output device, and/or tactile output device (e.g. vibrations, etc.)

An input device 975 may be coupled to the bus 960. The input device 975 may be an alphanumeric input device, such as a keyboard including alphanumeric and other keys, for enabling a user to communicate information and command selections to processing unit 910. An additional user input device 980 may further be included. One such user input device 980 is cursor control device 980, such as a mouse, a trackball, stylus, cursor direction keys, or touch screen, may be coupled to bus 940 through bus 960 for communicating direction information and command selections to processing unit 910, and for controlling movement on display device 970.

Another device, which may optionally be coupled to computer system 900, is a network device 985 for accessing other nodes of a distributed system via a network. The communication device 985 may include any of a number of commercially available networking peripheral devices such as those used for coupling to an Ethernet, token ring, Internet, or wide area network, personal area network, wireless network or other method of accessing other devices. The communication device 985 may further be a null-modem connection, or any other mechanism that provides connectivity between the computer system 900 and the outside world.

Note that any or all of the components of this system illustrated in FIG. 9 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 920, mass storage device 930, or other storage medium locally or remotely accessible to processor 910.

It will be apparent to those of ordinary skill in the art that the system, method, and process described herein can be implemented as software stored in main memory 920 or read only memory 950 and executed by processor 910. This control logic or software may also be resident on an article of manufacture comprising a computer readable medium having computer readable program code embodied therein and being readable by the mass storage device 930 and for causing the processor 910 to operate in accordance with the methods and teachings herein.

The present invention may also be embodied in a handheld or portable device containing a subset of the computer hardware components described above. For example, the handheld device may be configured to contain only the bus 940, the processor 910, and memory 950 and/or 920.

The handheld device may be configured to include a set of buttons or input signaling components with which a user may select from a set of available options. These could be considered input device #1 975 or input device #2 980. The handheld device may also be configured to include an output device 970 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 910, a data storage device 930, a bus 940, and memory 920, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 985.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 910. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A system comprising:
   receiving user identification data, the user identification data identifying each family member that may potentially be part of a sleep ecosystem and identifying a category of each family member, the categories comprising adult, child, and pet;
   a non-contact area motion sensor that does not contact family members sharing a sleep surface, the area motion sensor continually detecting movement data comprising movement or non-movement in each of a plurality of areas in a sleep area;
   a sleep ecosystem logic embodied in one or more non-transitory computer-readable media; and
   a processor coupled to the non-contact area motion sensor;
   wherein the sleep ecosystem logic, when executed by the processor, is to determine an identity of one or more of the family members sharing the sleep surface in the sleep area based on
   a) the continually detected movement data from the non-contact area motion sensor for the plurality of areas, the movement data detected over time and b) movement patterns for the identified categories of the family members, and wherein the determined identity is further based on c) a size indicated by the continually detected movement data and d) sizes for the identified categories of the family members, and wherein the identity of the one or more family members sharing the sleep surface defining a current sleep ecosystem, and
   (i) using the continually detected movement data to determine a sleep state of a first family member; (ii) using the sleep state of the first family member and an optimization criterion stored in a memory and based on at least one of historical sleep data of the first family member and user preferences of the first family member, to determine a first sleep parameter value for the first family member; (iii) to control an electronically-controllable device associated with the sleep area to adjust an environment affecting the first family member in the current sleep ecosystem in accordance with the first sleep parameter value of the first family member; (iv) using the continually detected movement data, determine a sleep state of a second family member; (v) adjust the first sleep parameter value to a second sleep parameter value based on the sleep state of the second family member; and (vi) control the electronically-controllable device to adjust the environment affecting the first family member and the second family member in the current sleep ecosystem in accordance with the second sleep parameter value.

2. The system of claim 1, further comprising:
   the area motion sensor comprising one or more selected from a group of: a passive infrared (PIR), proximity sensor (using radio waves, ultraviolet, or other sensors), microwave/radar sensor, area reflective sensor, ultrasonic sensor, accelerometer.

3. The system of claim 1, wherein:
   the area motion sensor to further detect movement;
   the sleep ecosystem logic to determine that a user is entering or exiting the sleep area, and updating the current sleep ecosystem to create an updated sleep ecosystem based on a determination by the sleep ecosystem logic that the user is entering or exiting the sleep area.

4. The system of claim 1, further comprising a body-worn motion sensor, the body-worn motion sensor data used in combination with the movement data from the non-contact area motion sensor to identify the one or more family members.

5. The system of claim 2,
   wherein the sleep ecosystem logic, when executed by the processor, adjusts environmental controls to optimize a sleep environment based on an identity of the one or more family members, and associated identification data about the one or more family members.

6. The system of claim 1, wherein the one or more family members are identified at a level of: a category, a subcategory, and an individual.

\* \* \* \* \*